US012649066B2

(12) United States Patent
Alviar et al.

(10) Patent No.: US 12,649,066 B2
(45) Date of Patent: Jun. 9, 2026

(54) MEDICAL DEVICE ACCESSORIES

(71) Applicant: Physio-Control, Inc., Redmond, WA (US)

(72) Inventors: Christopher G. Alviar, Seattle, WA (US); Jeremy Edward Brummett, Redmond, WA (US); Christopher William Egbert, Redmond, WA (US); Deniz Icingir, Kenmore, WA (US); Sarah Mynhier, Redmond, WA (US); Jeremy Wong, Redmond, WA (US); Neal Stanley Clark, Snohomish, WA (US); Barry D. Curtin, Seattle, WA (US); Suneethi Gudapati, Redmond, WA (US); Bethany J. Johnson, Kirkland, WA (US); Marc Mckissack, Redmond, WA (US); Marie Pahlmeyer, Redmond, WA (US); Brigitta M. Suwandana, Woodinville, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 18/599,831

(22) Filed: Mar. 8, 2024

(65) Prior Publication Data

US 2024/0207627 A1 Jun. 27, 2024

Related U.S. Application Data

(63) Continuation of application No. 17/206,276, filed on Mar. 19, 2021, now Pat. No. 11,951,322.
(Continued)

(51) Int. Cl.
*B65D 69/00* (2006.01)
*A61B 5/273* (2021.01)
(Continued)

(52) U.S. Cl.
CPC ............ *A61N 1/3968* (2013.01); *A61B 5/273* (2021.01); *A61B 5/33* (2021.01); *H01R 13/631* (2013.01)

(58) Field of Classification Search
CPC ................ A61N 1/3904; A61N 1/3968; A61B 2050/301; A61B 2050/311;
(Continued)

(56) References Cited

U.S. PATENT DOCUMENTS

| D136,560 | S | 10/1943 | Lebaigue |
| D152,530 | S | 2/1949 | Hampel |
| | | (Continued) | |

FOREIGN PATENT DOCUMENTS

| CN | 3412747 | 12/2004 |
| CN | 304648348 | 5/2018 |
| | (Continued) | |

OTHER PUBLICATIONS

Office Action for U.S. Appl. No. 29/865,346, mailed on Dec. 31, 2024, Brummett, "Medical Device Storage Bag", 6 pages.
(Continued)

*Primary Examiner* — Luan K Bui
(74) *Attorney, Agent, or Firm* — Lee & Hayes, P.C.

(57) ABSTRACT

Accessories of a medical device, such as a defibrillator, are described. The accessories reduce delays in treating or monitoring a patient by increasing the efficiency of using, and the ease of use of, the medical device. An adjustable kickstand is movable between a collapsed and extended position to recline the medical device. In the reclined position, a display of the medical device can be more easily viewed by the user. Storage bags can be coupled to the medical device to efficiently store accessories for use with the medical device. The stored accessories can be coupled to the medical device while the accessories are stored within
(Continued)

the storage bags. A port guard can protect and shield a connection between a cable and a port of the medical device to prevent the cable (e.g., an ECG cable) from being disconnected from the port of the medical device.

14 Claims, 19 Drawing Sheets

Related U.S. Application Data

(60) Provisional application No. 62/991,668, filed on Mar. 19, 2020.

(51) Int. Cl.
| | |
|---|---|
| *A61B 5/33* | (2021.01) |
| *A61N 1/39* | (2006.01) |
| *H01R 13/631* | (2006.01) |

(58) Field of Classification Search
CPC ... A61B 2050/3011; A61B 5/33; A61B 5/273; H01R 13/631; H01R 2201/12; B23P 19/04
USPC ...... 206/305, 320, 363, 438; 220/23.2, 23.4; 607/5
See application file for complete search history.

(56) References Cited

U.S. PATENT DOCUMENTS

| | | | |
|---|---|---|---|
| D162,845 S | 4/1951 | Kohn | |
| D224,074 S | 6/1972 | Harmon, Jr. | |
| D244,853 S | 6/1977 | Cordell, Jr. | |
| D257,079 S | 9/1980 | Globus | |
| D270,929 S | 10/1983 | Shasteen et al. | |
| D292,847 S | 11/1987 | Barker | |
| D327,167 S | 6/1992 | Franklin | |
| D351,281 S | 10/1994 | Petryk | |
| 5,409,153 A | 4/1995 | Ristich | |
| D360,015 S | 7/1995 | Cosby et al. | |
| 5,487,751 A | 1/1996 | Radons | |
| D367,173 S | 2/1996 | Trihus | |
| D375,197 S | 11/1996 | Laherty | |
| D382,705 S | 8/1997 | Tatsumi | |
| 5,766,042 A | 6/1998 | Ries et al. | |
| 5,808,865 A * | 9/1998 | Alves .................... | G06F 1/1628 |
| | | | 206/320 |
| D408,993 S | 5/1999 | Kliot | |
| D449,737 S | 10/2001 | Galliano | |
| 6,422,669 B1 * | 7/2002 | Salvatori .............. | A61N 1/3968 |
| | | | 206/320 |
| D466,688 S | 12/2002 | Hassett | |
| D525,027 S | 7/2006 | Higgins et al. | |
| D549,053 S | 8/2007 | Dellaferrera | |
| 7,316,313 B1 | 1/2008 | Juchau | |
| 7,320,420 B2 | 1/2008 | Buis et al. | |
| D613,941 S | 4/2010 | Daniel | |
| D623,398 S | 9/2010 | Meiser et al. | |
| D630,428 S | 1/2011 | Hong | |
| D639,050 S | 6/2011 | Bruhn | |
| D651,965 S | 1/2012 | Sanders | |
| D681,324 S | 5/2013 | Mohr | |
| D695,007 S * | 12/2013 | Zhang ............................ | D3/218 |
| D704,436 S | 5/2014 | Hickman | |
| D710,600 S | 8/2014 | Alamdar | |
| D710,602 S | 8/2014 | Alamdar | |
| D756,108 S | 5/2016 | Douglas, Jr. | |
| D767,877 S | 10/2016 | Halko | |
| D774,750 S | 12/2016 | Stark | |
| D781,110 S | 3/2017 | Jacobsen | |
| D784,014 S | 4/2017 | Scranton | |
| D796,189 S | 9/2017 | Zhang | |
| D796,194 S | 9/2017 | Scranton | |
| D797,445 S | 9/2017 | Boroski | |

| | | | | |
|---|---|---|---|---|
| D819,960 S | 6/2018 | Zhang | | |
| D830,691 S | 10/2018 | Guyot | | |
| D840,681 S | 2/2019 | Verver | | |
| D912,390 S | 3/2021 | Hyun | | |
| D919,962 S | 5/2021 | Shi | | |
| D937,567 S | 12/2021 | Eisenhardt et al. | | |
| D941,572 S | 1/2022 | Chiu et al. | | |
| D945,151 S | 3/2022 | Bietsch et al. | | |
| D945,312 S | 3/2022 | Michael et al. | | |
| D974,024 S | 1/2023 | Jang et al. | | |
| D977,243 S | 2/2023 | Brummett et al. | | |
| D1,008,752 S | 12/2023 | Wall | | |
| 2003/0036775 A1 | 2/2003 | Salvatori et al. | | |
| 2011/0005953 A1 | 1/2011 | Hochhalter | | |
| 2011/0275234 A1 | 11/2011 | Schmidt et al. | | |
| 2012/0150248 A1 | 6/2012 | Chi et al. | | |
| 2012/0271370 A1 | 10/2012 | Hochhalter et al. | | |
| 2014/0299486 A1 * | 10/2014 | Engimann, III | ....... | A61B 46/10 |
| | | | | 205/792 |
| 2016/0100887 A1 | 4/2016 | Wu et al. | | |
| 2016/0166321 A1 | 6/2016 | Amsler | | |
| 2017/0373447 A1 | 12/2017 | Schreiber et al. | | |
| 2021/0290968 A1 | 9/2021 | Alviar et al. | | |
| 2024/0207195 A1 | 6/2024 | Behl et al. | | |

FOREIGN PATENT DOCUMENTS

| | | |
|---|---|---|
| CN | 305294305 | 8/2019 |
| EP | 4287421 A2 | 12/2023 |
| IN | 365091-001 | 1/2023 |
| KR | 301109726.0000 | 5/2021 |
| KR | 3011502 | 2/2022 |
| KR | 301150229.0000 | 2/2022 |
| WO | 2015181767 A1 | 12/2015 |

OTHER PUBLICATIONS

Zoll, "Bedienerhandbuch", retrieved on Aug. 6, 2021 from <<https://www.defi.help/wp-content/uploads/2017/10/Bedienerhandbuch.pdf>>, Mar. 31, 2016, 48 pages.

Zoll X Series Carrying Case, retrieved Ap2 27, 2022, at <<https://coastbiomed.com/product/zoll-x-series-carrying-case/?gclid=EAlalQobCHMI1eqQkJvY9wlVk7JLCh00OgZuEAQYAiABEgJcm_D_BWE>>, 2022, 4 pgs.

Extended European Search Report mailed Aug. 16, 2021 for European Patent Application No. 21163663.4, 7 pages.

Extended European Search Report mailed Jan. 12, 2024 for European Application No. 232005579.8, a foreign counterpart to U.S. Appl. No. 17/206,276, 6 pages.

Johnson Level Mag Angle Locater 2 Button, retrieved Apr. 27, 2022, at <<https://www.lowes.com/pd.Johnson-Level-Magnetic-Digital-Angle-Locator/1000085673>>, 2017, 7 pgs.

Office Action for U.S. Appl. No. 17/206,276, mailed on Aug. 29, 2023, Christopher G. Alviar, "Medical Device Accessories", 9 pages.

Phoenixcontact, Plug Guard Security Frame—FL Plug Guard RD, retrieved on Aug. 6, 2021 from <<https://4donline.ihs.com/images/VipMasterIC/IC/PCON/PCON-S-A0000016077/PCON-S-A0000018134-1.pdf?hkey=52A5661711E402568146F3353EA87419>>, Oct. 10, 2014, 2 pages.

Physio Control Lifepak 15 TOUGH.flv, retrieved Apr. 27, 2022, at <<https://www.youtube.com/watch?=k7YZr5Lnq10&t=14S>>, 2010, 4 pgs.

Physio-Control, "Notice of Intent to Sole Source Award", retrieved on Aug. 6, 2021 from <<https://www.physio-control.com/uploadedFiles/Physio85/Contents/Healthcare_Professionals/Accessories_and_Disposals/LP15-Acc-Danish-3310824_D.pdf>>, Sep. 26, 2011, pp. 1-16.

Small Zippered Accessory Pouch, retrieved Apr. 27, 2022, at <<https://shednecks.com/marsupial-gear-small-zippered-accessory-pouch/>>, 2022, 4 pgs.

Camp County EMS Post, available at facebook.com, retrieved Jul. 6, 2024, at <<https://www.facebook.com/CampCountyEMS/posts/we-

(56)        References Cited

OTHER PUBLICATIONS just-received-8-new-lifepak-15-cardiac-monitordefibrillators-to-replace-our-l/1631919120204484>>, 1 pg.

Carry Case New For MRx Monitor/Defibrillator Vinyl Ea, available at henryschein. com, retrived Jul. 2024, at <<https://www.henryschein.com/us-es/medical/p/equipmenUcardiology/carrying-case-f-defib-complete/4995635>>, 2024, 2 pgs.

LifePak Brochure, retrieved Jul. 6, 2024, at <<chrome-extension ://efaidnbm nnnibpcajpcglclefi ndmkaj/https://www.transmed-USA.com/physio pdfs/lp 15/LI Fe Pak 15 Brochure_3301019_A.pdf>>, 2009, 20 pgs.

Office Action for U.S. Appl. No. 29/865,345, mailed on Jul. 16, 2024, Brummett, "Medical Device Storage Bag", 9 pages.

Office Action for U.S. Appl. No. 29/865,346, mailed on Jul. 16, 2024, Brummett, "Medical Device Storage Bag", 8 pages.

ZOLL—Defibrillator Monitor IX Series, available at medicalsearch.com.au, retrieved Jul. 6, 2024, at <<https://www.medicalsearch.com.au/zoll-defibrillator-monitor-x-series/p/159396>>,2024, 1 pg.

* cited by examiner

321

320

322

320

324

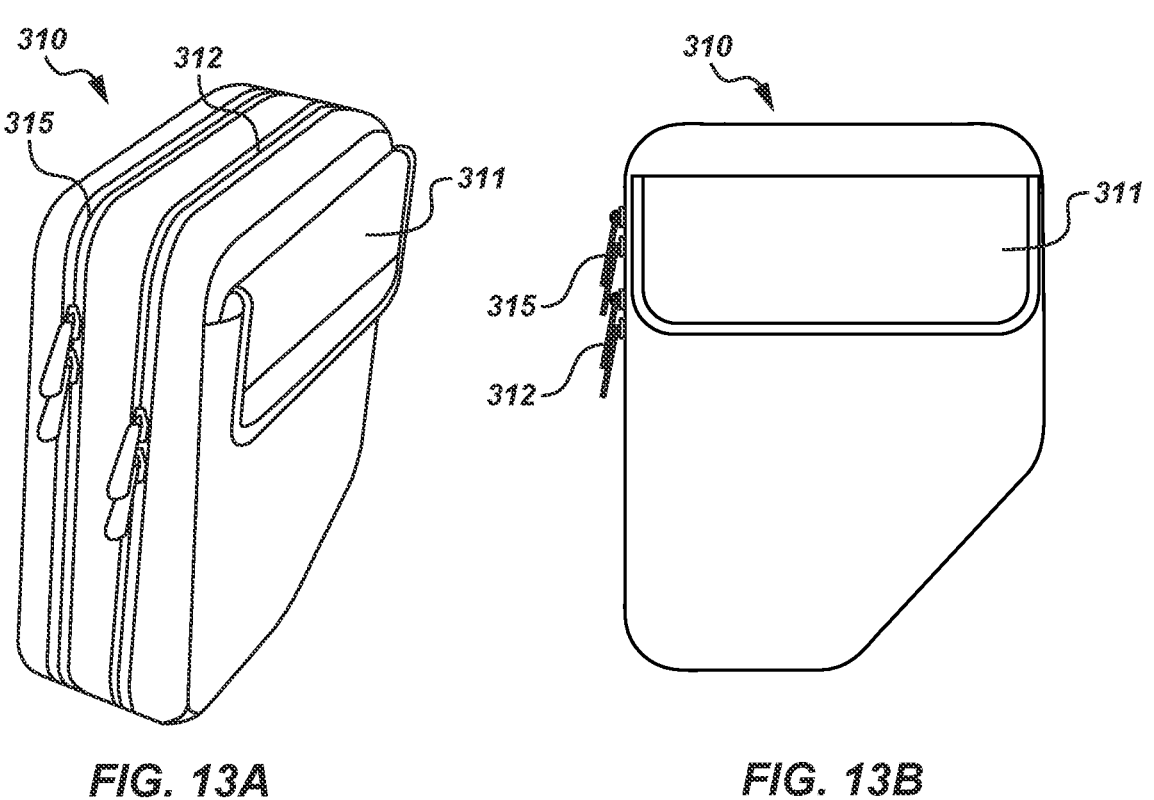
*FIG. 13A*
*FIG. 13B*
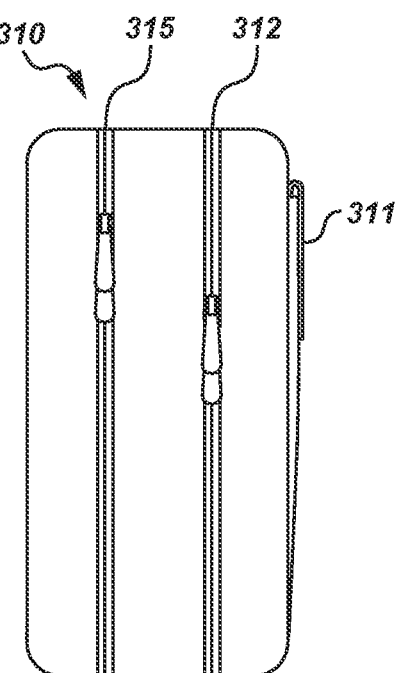
*FIG. 13C*
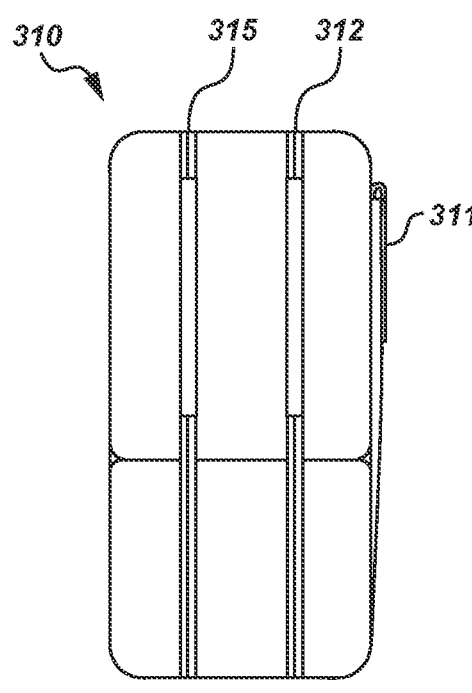
*FIG. 13D*

MEDICAL DEVICE ACCESSORIES

CROSS-REFERENCE TO RELATED APPLICATIONS

This application is a continuation of U.S. patent application Ser. No. 17/206,276, titled "Medical Device Accessories" and filed on Mar. 19, 2021, which claims the benefit of U.S. Provisional Application No. 62/991,668, titled "Medical Device Accessories" and filed on Mar. 19, 2020, each of which is incorporated by reference herein in its entirety.

BACKGROUND

A medical device, such as a monitor-defibrillator, is usable to monitor and treat a patient at an emergency scene. The medical device is typically moved with the patient as the patient is transported along a chain of care from the emergency scene to a medical facility, such as an emergency room at a hospital. For example, the patient is first treated by emergency responders, such as paramedics, and then transported to a treatment facility, such as a hospital. When treating a patient, emergency responders receive information regarding the patient from multiple sources, such as from their own observations of the patient and their surroundings, from bystanders, from other responders, and from one or more medical devices being used to monitor and treat the patient. It is mentally taxing for emergency responders to process the incoming patient information and prioritize tasks. In addition, it may be time-consuming for emergency responders to find the appropriate accessories, such as cables, sensors, and treatment components, let alone couple those accessories to the medical device before they are usable to help monitor or treat the patient.

During monitoring or treatment of a patient, depending on where the medical device is placed, it is sometimes difficult for the emergency responder(s) to see the information presented on the display of the medical device. Moreover, movement of the medical device can cause cables to disconnect from the medical device. As an illustrative example, if an electrocardiogram (ECG) cable is inadvertently disconnected from a defibrillator, the defibrillator no longer receives ECG data regarding the patient, which effectively "blinds" the defibrillator for a period of time until the ECG cable is reconnected. Even after reconnecting the ECG cable, there can be a delay as the defibrillator reacquires the ECG signal and receives enough ECG data to assess the physiological state of the patient. Such a delay can hinder patient treatment and monitoring. The disclosure made herein is presented with respect to these and other considerations.

BRIEF DESCRIPTION OF THE DRAWINGS

FIG. 13A illustrates a perspective view of an example storage bag for a medical device.

FIG. 13B illustrates a front view of the example storage bag depicted in FIG. 13A.

FIG. 13C illustrates a side view of the example storage bag depicted in FIG. 13A.

FIG. 13D illustrates another side view of the example storage bag depicted in FIG. 13A.

DETAILED DESCRIPTION

Figure 1A:
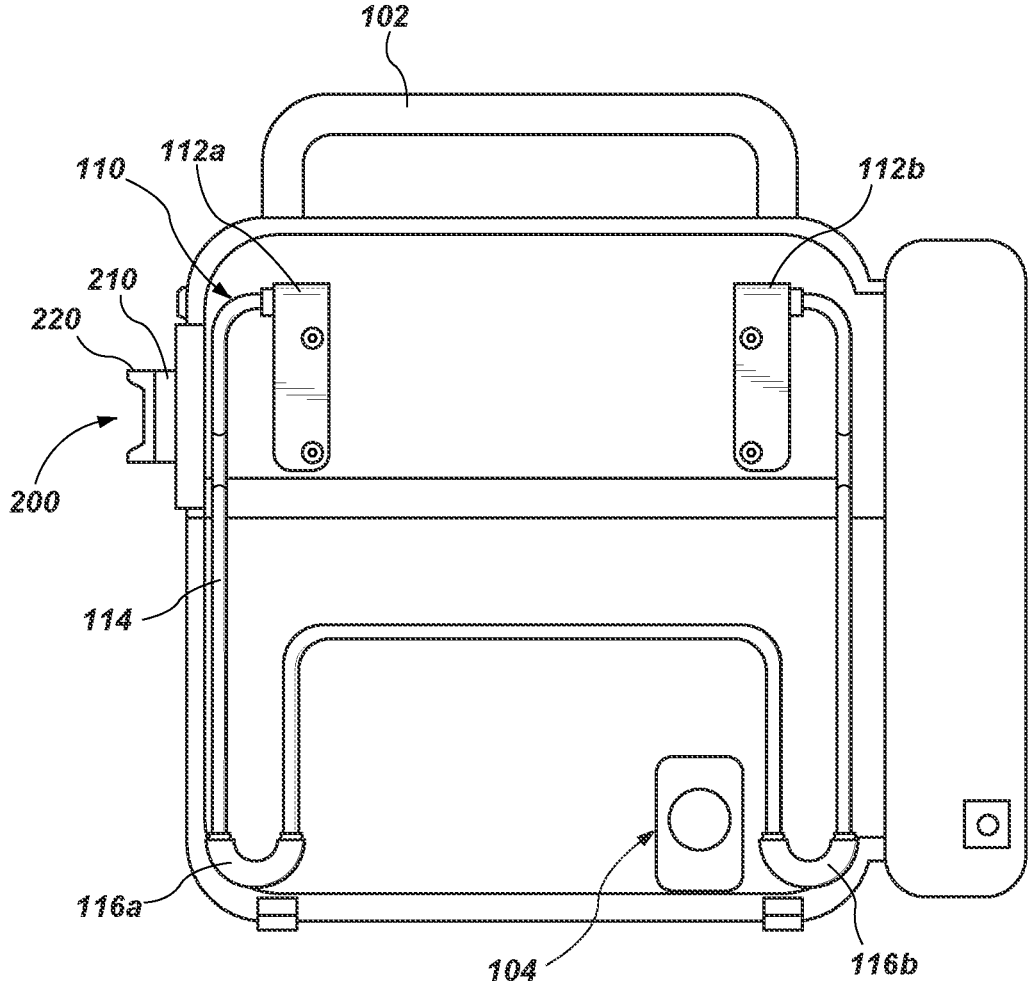
FIG. 1A illustrates a rear view of an example medical device having an example kickstand coupled thereto, the kickstand in a collapsed position in FIG. 1A.

Delays in treating or monitoring a patient can adversely affect an outcome of the patient, especially in an emergency medical setting like a patient experiencing a cardiac event away from a hospital. The disclosure provides medical device accessories that, when used with a medical device, reduce delays in using the medical device to treat and/or monitor a patient, and increase the ease and efficiency of using the medical device. Various implementations described herein relate to medical device accessories that permit users, such as rescuers or first responders, to more efficiently, conveniently, and effectively monitor and/or treat a patient during a medical event. The increased efficiency, convenience, and effectiveness of patient monitoring and/or treatment contributes to improved patient outcomes in situations when timeliness is a critical factor, such as during cardiac events.

An example accessory described herein is an adjustable kickstand that is configured to be coupled to a medical device. In some examples, the medical device has a display on a first surface (e.g., a front surface) of the medical device, and the kickstand is coupled to a second, opposite surface (e.g., a rear surface) of the medical device. The kickstand is movable between a collapsed (or stowed) position to one or more extended positions. When not in use, the disclosed adjustable kickstand is collapsed to the collapsed position, minimizing its occupied space, and thus maintaining a slim and compact overall footprint of the medical device with the kickstand coupled thereto. The adjustable kickstand is extendable from the collapsed position to an extended position where a portion of the kickstand is spaced away from the medical device. In this extended position, the kickstand supports the medical device in a reclined orientation to allow the user to more readily view the display of the medical device. In some examples, the kickstand includes a support that is configured to be pivotably coupled to the medical device at respective ends of the support, and the support includes a pair of feet coupled to the ends of the support, the pair of feet configured to contact a surface on which the medical device rests when the kickstand is in the extended position. Without the adjustable kickstand, the user is limited in his/her ability to orient the medical device and, hence, the display thereof. Placement of the medical device is oftentimes limited at an emergency event due to space constraints and environmental barriers, such as the terrain or location where the patient experiences the emergency event. Oftentimes, none of the possible placements of the medical device provides an adequate orientation for the user to easily view the display. Using the disclosed adjustable kickstand, the user can recline the medical device, which increases the possible orientations at which the user can position the medical device and its display to optimize or improve his/her view of the display. This can allow the user, such as a responder, to position the medical device so that the user can more effectively receive and process the information being relayed by the medical device via the display thereof.

Other example accessories described herein include storage bags for efficiently storing and organizing various other accessories of the medical device. For example, storage bags are configured to be coupled to the medical device such that the medical device and the storage bags coupled thereto can be moved and transported as a unit. Various accessories, such as cables, sensors, durables, and/or consumables that are usable with the medical device, are stored within the storage bags in an organized manner. The storage bags can include interior organizational elements and features, such as pockets, shelves, dividers and/or other organizational elements to assist with organizing the contents of the storage bags for efficient access by a user. The storage bags may assist with organizing cables and other accessories of the medical device, which allows the accessories to be located and accessed rapidly. Additionally, the storage bags can allow the accessories contained within the storage bags to be coupled to the medical device while in storage. For example, a storage bag may include an opening defined in a portion of the storage bag, which is configured to allow an accessory to be coupled to the medical device while the accessory is stored within the interior of the storage bag and while the storage bag is closed. In this manner, the accessories can be quickly deployed and used when the medical device is transported to a patient event, seeing as how the stored accessories are already coupled to the medical device and ready to use with the medical device.

Another example accessory described herein is a port guard positioned about or around a port of the medical device and protruding from an exterior surface of the medical device to prevent or minimize a potential disconnection of a cable, such as an ECG cable, from the port of the medical device. For example, during treatment or monitoring of a patient using a medical device, disconnection of the ECG cable from a port of the medical device can prevent the medical device from analyzing the ECG signal of the patient, which causes delays in treating or monitoring the patient. The port guard described herein is configured to prevent or minimize a potential disconnection of a cable, such as an ECG cable, from a port, such as an ECG port, of the medical device. In general, the medical device accessories described herein increase the efficiency and ease of use of the medical device, which allows the user of the medical device to focus on, and tend to, the patient more efficiently and effectively.

Figure 1B:
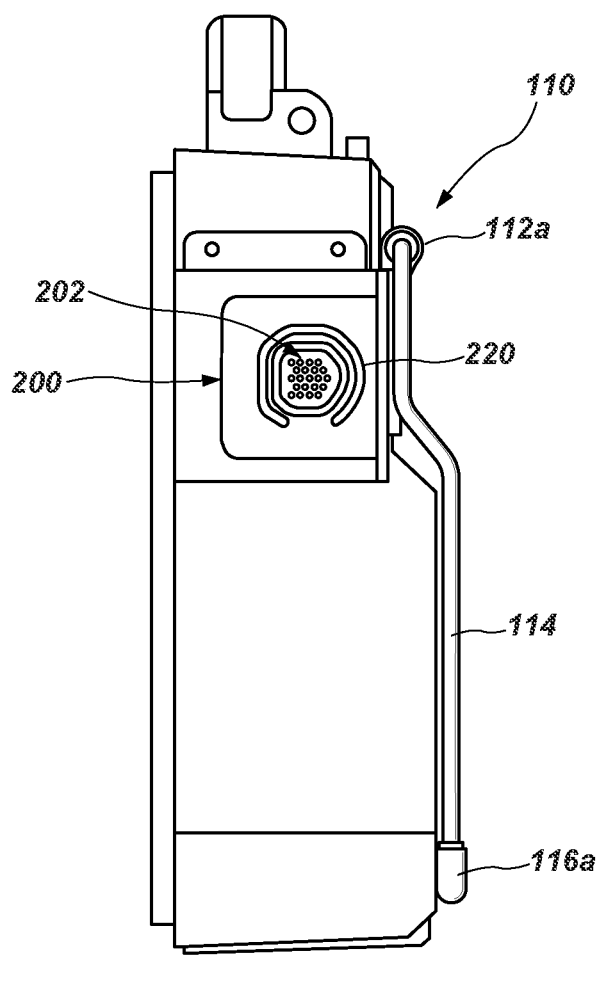
FIG. 1B illustrates a side view of the example medical device and kickstand depicted in FIG. 1A.
Figure 1C:
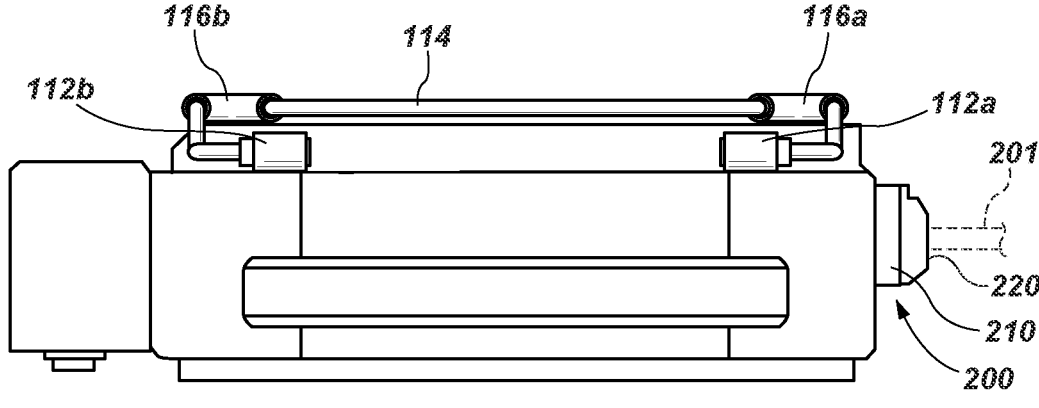
FIG. 1C illustrates a top view of the example medical device and kickstand depicted in FIG. 1A.
Figure 1D:
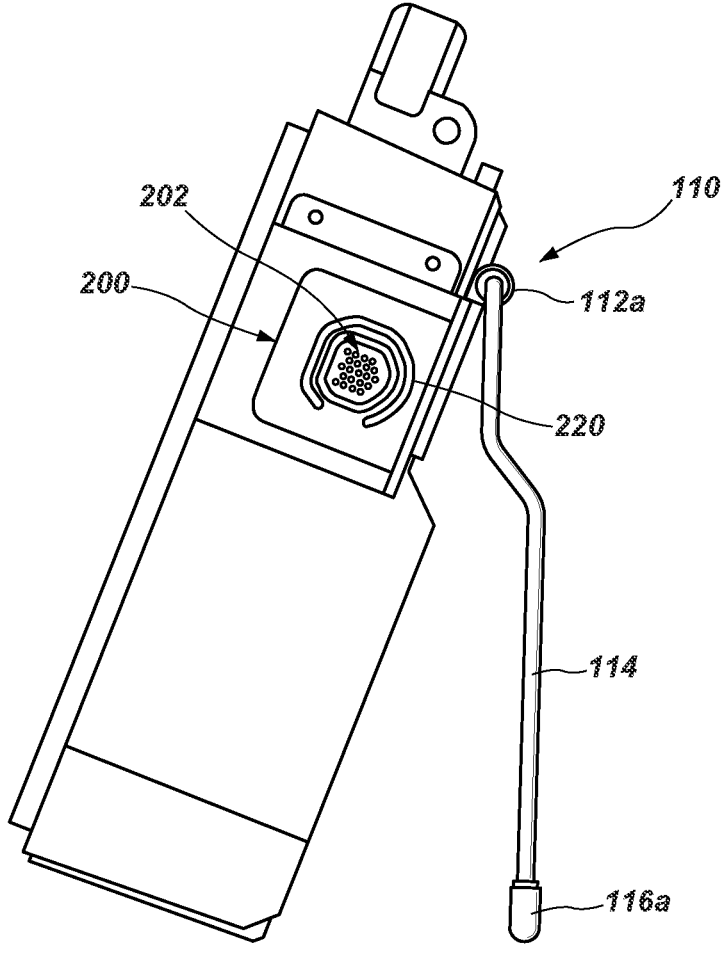
FIG. 1D illustrates a side view of the example medical device depicted in FIG. 1A with the kickstand in an extended position.
Figure 1E:
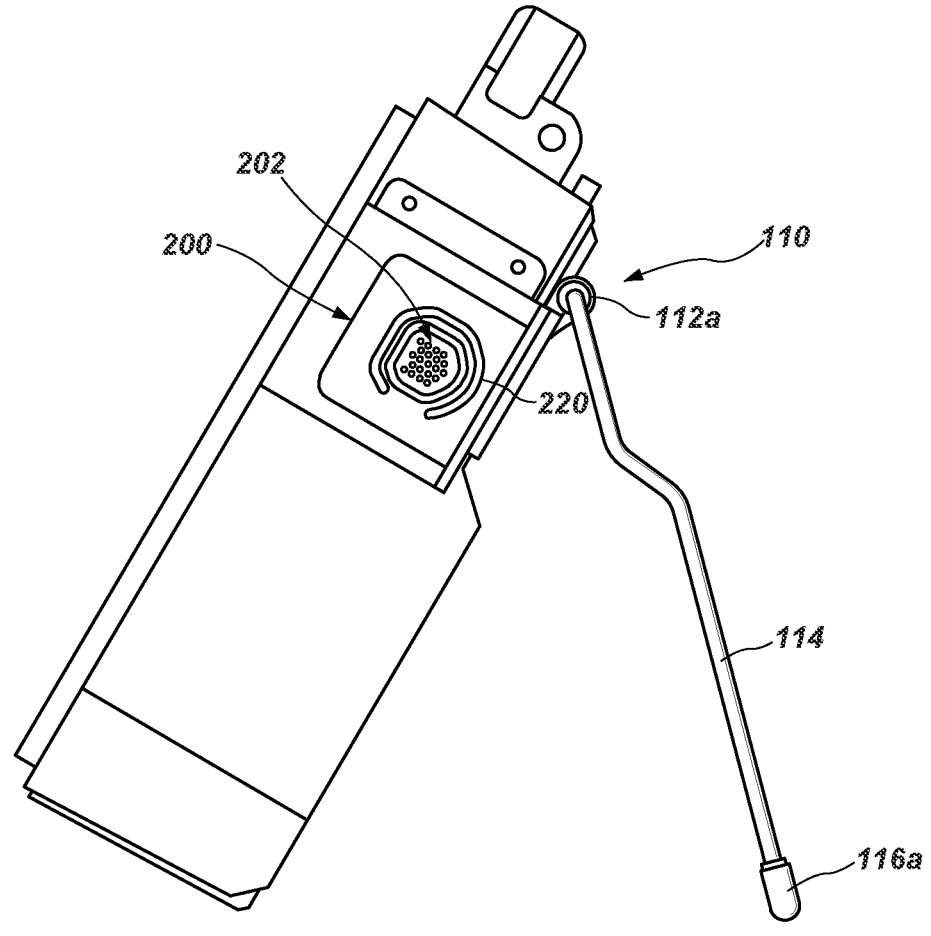
FIG. 1E illustrates a side view of the example medical device depicted in FIG. 1A with the kickstand in another extended position, such as a maximum extended position.

Turning now to FIGS. 1A-1E, an example medical device 102 is shown. In this example, the medical device 102 has an example kickstand 110 coupled thereto. FIG. 1A illustrates a rear view of the medical device 102 having kickstand 110 (in a collapsed position) coupled thereto. FIG. 1B illustrates a side view of the same, and FIG. 1C illustrates a top view of the same. FIG. 1D illustrates a side view of the medical device 102 with the kickstand 110 in an extended position (e.g., a first, intermediate extended position), while FIG. 1E illustrates a side view of the medical device 102 with the kickstand 110 in another extended position (e.g., a second, maximum extended position).

The medical device 102 is configured to be implemented as any suitable type of medical device 102, such as an emergency medical device having a display. The medical device 102 in FIGS. 1A-1E is, by way of example, depicted as a defibrillator, such as a monitor-defibrillator, with the display 301 (See FIG. 6A) positioned on a front of the medical device 102. The medical device 102 can include various electrical components to assist with monitoring and/or treating a patient. The various electrical components of the medical device 102 can be contained within a hollow interior of a housing of the medical device 102. The display 301 (e.g., on the front of the medical device 102) in this example is configured to output patient information for viewing by a user of the medical device 102, such as a rescuer. Without the disclosed kickstand 110, the display 301 of the medical device 102 can be difficult or inconvenient for the user to view properly when the medical device 102 is in certain orientations. For example, if the medical device 102 is sitting upright on a surface, the base (or bottom surface) of the medical device 102 rests flat on the surface, and the display 301 is oriented orthogonally to the surface. Depending on the user's position or orientation relative to the medical device 102, the user may be unable to adequately view the display 301 without having to reposition or reorient themselves and/or the medial device 102. During medical emergencies, such as cardiac events, minutes, and sometimes even seconds, can improve a patient's outcome. The adjustable kickstand 110 disclosed herein is movable between a collapsed position and one or more extended positions to allow a user to position the medical device 102 and the display 301 at any suitable angle or orientation among multiple different angles or orientations. For example, the user may recline the medical device 102 into a reclined orientation to improve the user's view of the display 301 of the medical device 102. Accordingly, the adjustable kickstand 110 allows a user of the medical device 102 to more efficiently and effectively monitor or treat the patient using the medical device 102.

FIGS. 1A-1C show the adjustable kickstand 110 in the collapsed position. In the collapsed position, the adjustable kickstand 110 lays against (e.g., touches, abuts, etc.) or near (e.g., adjacent, next to, etc.) a rear surface of the medical device 102. In the example of FIGS. 1A-1E the adjustable kickstand 110 is configured to be rotated or pivoted about an axis of rotation associated with a pair of hinges 112. For example, the hinges 112 act as the center point of rotation for the kickstand 110. When the kickstand 110 is moved from the collapsed position into an extended position, the kickstand 110 is moved (e.g., rotated about the axis of rotation) away from the rear surface of the medical device 102. In the extended position (e.g., See FIGS. 1D and 1E), the kickstand 110 is configured to support the medical device 102 at a reclined angle. The adjustable kickstand 110 can be moveable to multiple extended positions to allow the user to adjust the inclined orientation of the medical device 102, such as to a rescuer's desired inclination. In an example, the adjustable kickstand 110 is configured to be positioned to an angle among multiple different angles by extending the adjustable kickstand 110 to any position between the collapsed position and a maximum extended position. Alternatively, the adjustability can be preset, with the adjustable kickstand 110 moveable between the collapsed position and one or more preset extended positions, such as a maximum extended position and/or one or more intermediate positions between the collapsed position and the maximum extended position.

In this example, the adjustable kickstand 110 includes a hinge element 118a configured to resist rotation of the adjustable kickstand 110 when the adjustable kickstand 110 is moved into an extended position, such as one of multiple preset extended positions. By constraining rotation of the adjustable kickstand 110 in the extended position(s), the adjustable kickstand 110 is prevented from collapsing or rotating in an unintended or unwanted manner. The hinge element 118a is configured to maintain the kickstand 110 in the collapsed position and/or a particular extended position.

In FIGS. 1A-1E, the adjustable kickstand 110 includes a support 114 (sometimes referred to herein as a "stand 114" or a "bent element 114"). The support 114 may be in the form of a rod, bar, wire, pipe, or tube. In these examples, the pair of hinges 112a, 112b are coupled to the rear of the medical device 102, and the respective ends of the support 114 are coupled to (e.g., rotatably coupled to, pivotably coupled to, retained in, etc.) the pair of hinges 112a, 112b. In this example, the support 114 is shaped and bent to follow a profile of the rear of the medical device 102, which may be contoured, so that the support 114 is positioned proximal to the rear of the medical device 102 in the collapsed position, and so that a distance the collapsed adjustable kickstand 110 protrudes from the rear of the medical device 102 is minimized. The support 114 can substantially conform to a profile of the rear surface of the medical device 102. In other words, the profile of the support 114 may have a similar contour or shape to that of the profile of the rear surface of the medical device 102.

In FIGS. 1A-1E, the support 114 is shaped and bent to extend, from a first hinge 112a positioned at the top of the rear surface of the medical device 102, in a horizontal direction towards a side surface of the medical device 102. The support 114 then curves at a 90 degree (°) elbow downward as a vertically-oriented support bar that extends vertically next to the side surface and along the rear profile of the medical device 102 towards a lower surface or bottom of the medical device 102. Near the bottom of the medical device 102, the support 114 loops back on itself to form a first u-shaped foot 116a that is positioned vertically away (e.g., inset) from the base (or bottom surface) of the medical device 102 so that first foot 116a of the adjustable kickstand 110 does not contact a horizontal surface on which the medical device 102 rests when the kickstand 110 is in the collapsed position. From the first u-shaped foot 116a, the support 114 extends vertically upwards along the profile of the rear surface of the medical device 102 for a distance and then curves at another 90° elbow and extends horizontally as a horizontally-oriented cross bar along the rear surface of the medical device 102 towards the other side surface of the medical device 102.

The support 114 is then mirrored along the other half of the medical device 102, curving at another 90° elbow and extending downwards again towards the base (or bottom surface) of the medical device 102 and looping back on itself again to form a second u-shaped foot 116b that is also inset from the bottom surface, and then extending vertically upwards as another vertically-oriented support bar next to the other side surface and along the rear surface of the medical device 102, and then curving inwards again at another 90° elbow into a second hinge 112b positioned at the top of the rear surface of the medical device 102. Thus, two ends of the support 114 point inward, are spaced apart from each other, and face each other. When the kickstand 110 is in the collapsed position, the pair of feet 116a, 116b are positioned near the base of the medical device 102, and the first foot 116a is positioned near a first side of the medical device 102 while the second foot 116a is positioned near a second, opposite side of the medical device 102. In other words, the pair of feet 116a, 116b straddle an imaginary centerline that runs vertically through the medical device 102. The distance between the first foot 116a and the second foot 116b, and the symmetry of the feet 116a, 116b about the center of the medical device 102 provides stability when the kickstand 110 is deployed and used to support the medical device 102 in a reclined orientation. The various portions of the support 114 can be separate elements, such as side elements that extend between the hinges 112a, 112b and feet 116a, 116b, and another element that extends between the first foot 116a and the second foot 116b. Alternatively, the support 114 can be a continuous element (e.g., a single, continuous bent rod) that is bent or formed into the desired shape for the adjustable kickstand 110. It will be appreciated that although in this example the support 114 is bent at 90° (and 180°)angles at the top and bottom, other angles can be envisaged.

In the examples, the first hinge 112a is mounted to the back of the medical device 102 within an upper left quadrant of the back of the medical device 102, as depicted in FIG. 1A. In these examples, the second hinge 112b is mounted to the back of the medical device 102 within an upper right quadrant of the back of the medical device 102, as depicted in FIG. 1A. To couple the respective ends of the support 114 to the hinges 112a, 112b, each end of the support 114 is inserted into an opening or cavity defined in a corresponding hinge 112a, 112b. In an example, the ends of the support 114 are shaped so that the ends of the support 114 are spaced apart a similar distance as a distance between the hinges 112a, 112b. The support 114 can be flexible and resilient such that the ends of the support 114 are configured to be flexed apart to allow the ends of the support 114 to be placed into the hinges 112a, 112b and then the support 114 can be released, causing the resilient support 114 to return to an initial, relaxed state with the ends of the support 114 now inserted within the respective openings defined in the hinges 112a, 112b. In other examples, one or more components are configured to be coupled to the ends of the support 114 to retain the ends of the support 114 to or within the hinges 112a, 112b. By the coupling of the ends of the support 114 to the hinges 112a, 112b, the ends of the support 114 are rotatably or pivotably coupled to the back of the medical device 102. For example, the first end of the support 114 is pivotably coupled to the back of the medical device 102 (e.g., the first end may be pivotably coupled to the first hinge 112a), and the second end of the support 114 is pivotably coupled to the back of the medical device 102 (e.g., the second end may be pivotably coupled to the second hinge 112b). This pivotable coupling allows the support 114 to be moved relative to the medical device 102 to transition the kickstand 110 between a collapsed position and one or more extended positions. As used herein, the term "couple" may refer to an indirect coupling or a direct coupling between elements. The term "couple," as used herein, may also refer to a removable coupling or a permanent coupling between the elements. Elements are removably coupled if a user or another entity is able to decouple the elements. Elements are permanently coupled if a user or another entity is unable to decouple the elements without destroying or significantly damaging the elements, or without undue effort to dissemble the elements using tools or machinery. As used herein, the term "couple" can be interpreted as connect, attach, join, engage, interface, link, fasten, or bind. Unless otherwise specified herein, the term "couple" is to be interpreted as coupling elements in a mechanical sense, rather than in an electrical sense, for example. Nevertheless, it is to be appreciated that a mechanical coupling of elements may result in an electrical coupling(s) between multiple elements of the system.

As mentioned, the adjustable kickstand 110, in some examples, includes feet 116a and 116b coupled to the respective ends of the support 114 and configured to contact a surface on which the medical device 102 rests when the adjustable kickstand 110 is in an extended position. The feet 116a and 116b help prevent unwanted movement of the medical device 102 along the surface and the unintended movement of the adjustable kickstand 110 from its current extended position. When the adjustable kickstand 110 is in the collapsed position, the feet 116a and 116b of the adjustable kickstand 110 are spaced away (e.g., inset) from a base (or bottom surface) of the medical device 102 and do not contact the surface on which the base of the medical device 102 rests when the medical device 102 is upright-oriented on the supporting surface (e.g., the ground, a table, a counter, etc.). Furthermore, when the kickstand 110 is in the collapsed position, the first foot 116a is disposed adjacent to a lower left quadrant of the back of the medical device 102, as depicted in FIG. 1A, and the second foot 116b is disposed adjacent to a lower right quadrant of the back of the medial device 102.

In some examples, the pair of feet 116a, 116b are the u-shaped portions of the support 114 or any other portions thereof. In some examples, the feet 116a, 116b are individual elements to which portions of the support 114 are attached, such as inserted into the feet 116a, 116b. Alternatively, in other examples, the feet 116a, 116b are slid over portions of the support 114, such as the u-shaped portions, and retained in place. In an example, the feet 116a, 116b are hollow rubber tubes that are slid along or about the support 114 into position about the u-shaped portions of the support 114 at the bottom of the rear surface of the medical device 102.

The feet 116a, 116b of the adjustable kickstand 110 are configured to contact a surface (e.g., the ground, a table, a counter, etc.) when the adjustable kickstand 110 is positioned in the extended position. In some examples, the feet 116a, 116b are made of a higher friction material than a remainder of the support 114 and are configured to prevent movement, such as sliding, of the medical device 102 and/or the adjustable kickstand 110 along a surface. This is, at least in part, due to the additional friction provided by material of the feet 116a, 116b. Accordingly, the feet 116a, 116b are sometimes referred to as herein as "non-slip elements 116." The increased friction also prevents the adjustable kickstand 110 from collapsing when the kickstand 110 is in the extended position and the medical device 102 is reclined. Additional feet can be included on the housing of the medical device 102 (e.g., on a bottom surface or edge at the base of the medical device 102) to further assist with preventing unwanted movement (e.g., sliding, slipping, etc.) of the medical device 102 along a surface upon which the medical device 102 rests.

As shown in FIGS. 1B and 1C, the support 114 of the adjustable kickstand 110 substantially conforms to a profile of the rear surface of the medical device 102, which is contoured, when the kickstand 110 is in the collapsed position. Further, the feet 116a, 116b of the adjustable kickstand 110 do not contact a surface upon which the base of the medical device 102 rests when the adjustable kickstand 110 is in the collapsed position, such as shown in FIGS. 1A and 1B. That is, the medical device 102 is self-supporting (without the aid of the kickstand 110) in a vertical, upright orientation as shown when the adjustable kickstand 110 is in the collapsed position. With the adjustable kickstand 110 in the collapsed position (e.g., when the adjustable kickstand 110 is stowed, abutting or next to the rear surface of the medical device 102), the adjustable kickstand 110 does not support any of the weight of the medical device 102.

When the adjustable kickstand 110 is in an extended position, such as shown in FIGS. 1D and 1E, the feet 116a, 116b and a portion of a base of the medical device 102 contact the surface upon which the medical device 102 rests in the reclined orientation. In the reclined orientation, the medical device 102 is supported by both the adjustable kickstand 110 and the portion of the base of the medical device 102. That is, the weight of the medical device 102 is distributed on the surface by the extended kickstand 110 partially supporting the weight of the medical device 102. This is unlike the collapsed position of the adjustable kickstand 110, in which the kickstand 110 does not support any of the weight of the medical device 102. The adjustable kickstand 110 is movable from the collapsed position to one or more extended positions, such as shown in FIGS. 1D and 1E.

The multiple extended positions in which the kickstand 110 is placeable allow the user to adjust the reclined orientation of the medical device 102 to a preferred orientation. To assist in supporting the medical device 102, the adjustable kickstand 110 is constructed of a suitable material to support the weight of the medical device 102. In this example, the adjustable kickstand 110 is a bar or a rod constructed of metal, such as steel, that is bent, forged and/or cast into the desired size and shape. Alternatively, in some examples, the adjustable kickstand 110 is constructed of a hollow metal pipe or tube that is bent into the desired size and shape. Thus, the support 114 of the kickstand 110, in some examples, may be a bent, metal bar, rod, pipe, or tube. In other examples, the adjustable kickstand 110 is constructed of other suitable material, such as a polymer, composite, and/or other material.

Figure 2:
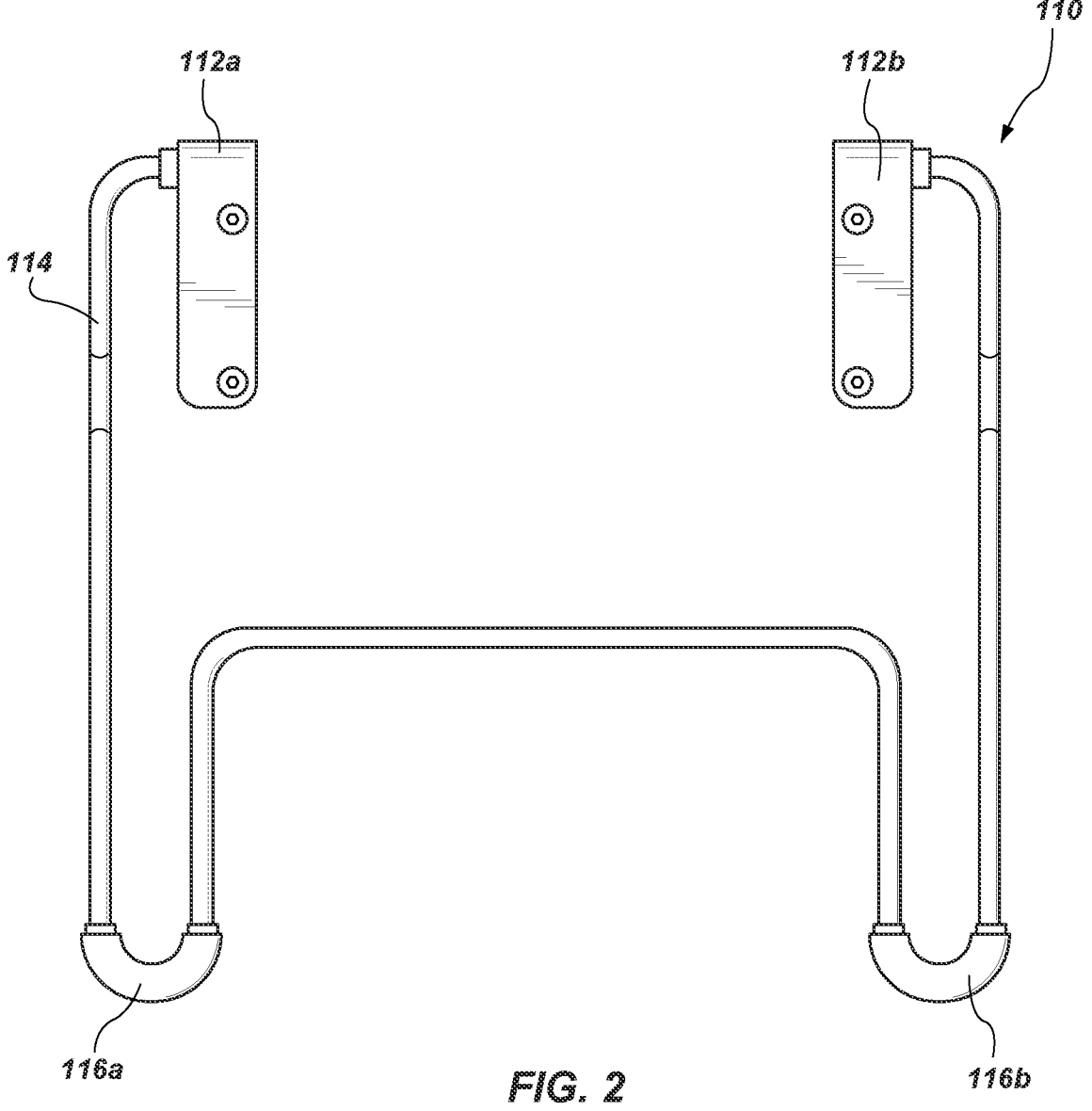
FIG. 2 illustrates the example kickstand depicted in FIG. 1A, the kickstand in FIG. 2 being decoupled from the medical device.

FIG. 2 illustrates the example adjustable kickstand 110 that includes the hinges 112a, 112b, and the support 114 including the feet 116a, 116b. The adjustable kickstand 110 is configured to be coupled to the medical device 102 by the hinges 112a, 112b, which are configured to be mounted to the medical device 102, such as by fasteners or an adhesive. The support 114 is rotatable relative to the medical device 102 about an axis that runs horizontally through the top portions (e.g., through the openings) of the hinges 112a, 112b where the respective ends of the support 114 are received. This ability of the support 114 to rotate relative to the medical device 102 allows the medical device 102 to be reclined, and it allows the weight of the medical device 102 to be at least partially supported by the adjustable kickstand 110, such as when the adjustable kickstand 110 is in an extended position. The feet 116a, 116b are configured to contact a surface on which the medical device 102 is positioned when the adjustable kickstand 110 is in the extended position to prevent motion of the reclined medical device 102 across the surface. This motion is prevented due to the friction provided by the material of the feet 116a, 116b. The force of friction provided by the material of the feet 116a, 116b is greater than a force perpendicular to a normal force on the kickstand 110, thereby preventing the kickstand 110 from slipping on the surface.

The support 114 of the adjustable kickstand 110 is shaped to form the u-shaped portions corresponding to the feet 116a, 116b of the support 114, and which are configured to support the medical device 102 when the adjustable kickstand 110 is in an extended position. The portion of the support 114 that extends upward from the feet 116a, 116b may be referred to as the "legs" of the support 114, which, in some examples, are shaped so as to not hinder user access to portions of the rear of the medical device 102 when the adjustable kickstand 110 is in the collapsed position. For example, in FIG. 1A the "legs" of the support 114 extend around a power connector 104 on the back of the medical device 102 to avoid obstructing the power connector 104 when the adjustable kickstand 110 is in the collapsed position. Additionally, the horizontal portion of the support 114 extending between the two "legs" (sometimes referred to herein as a "cross bar" of the support 114) can be configured to support one or more accessories, as will be discussed in more detail below. In some examples, the support 114 extends horizontally near the bottom (e.g., along a bottom edge) of the medical device 102 so that the support 114 forms a "u-shape" from the hinge 112a to the hinge 112b. In these examples, the adjustable kickstand 110 is configured to support the medical device 102 by a horizontal portion of the support 114 that is configured to contact the surface on which the medical device 102 rests when the adjustable kickstand 110 is in an extended position. In other words, the center horizontal cross bar of the kickstand 110 may not be offset vertically from the feet 116a, 116b, and may instead be closer to a bottom of the medical device 102 such that the entire center horizontal portion of the kickstand 110 is configured to contact a surface on which the medical device 102 rests.

Figure 3:
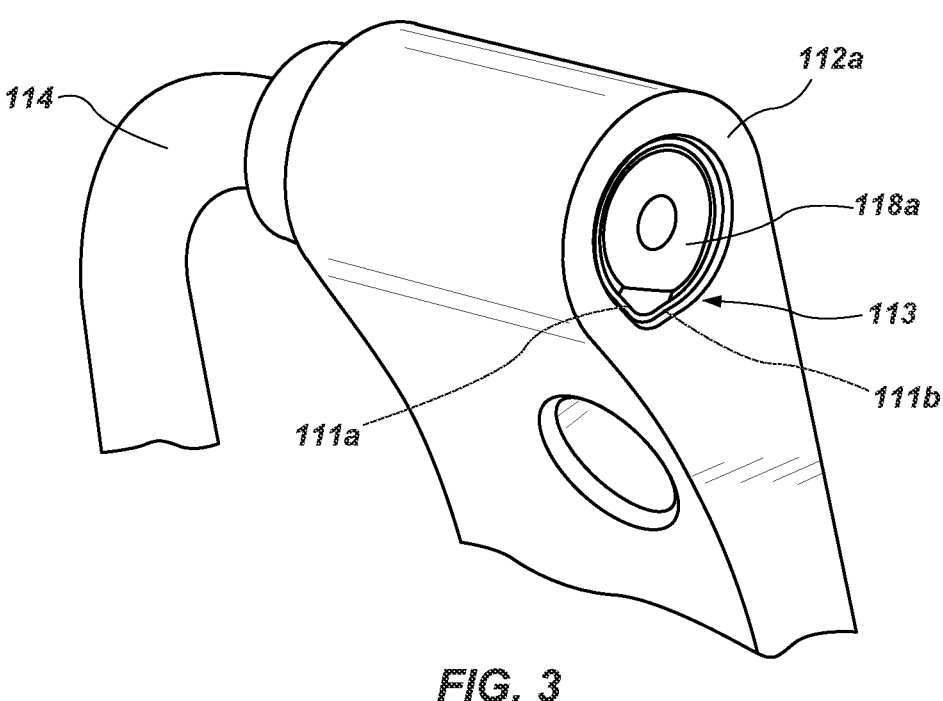
FIG. 3 illustrates a detailed view of a portion of an example hinge of the kickstand and a first end of a support of the kickstand depicted in FIG. 2.
Figure 4:
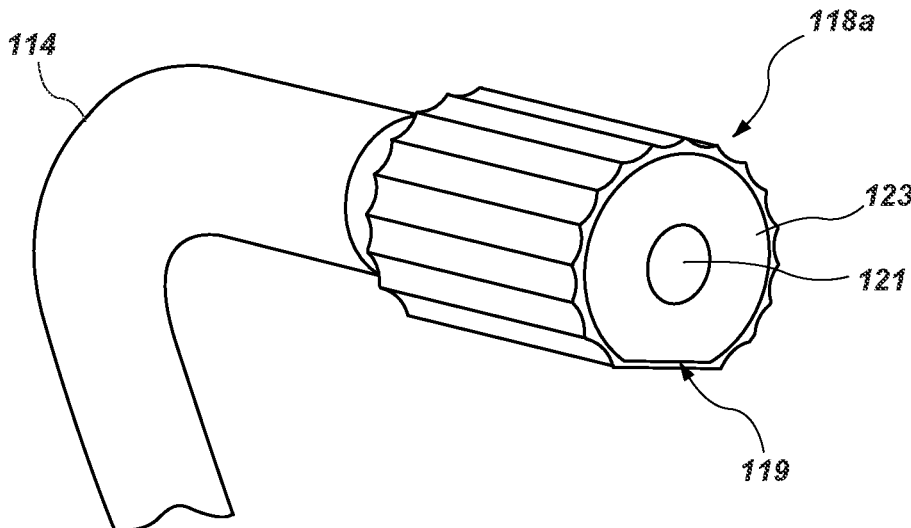
FIG. 4 illustrates a detailed view of an example hinge element of the kickstand depicted in FIG. 2.

FIG. 3 illustrates a detailed view of a portion of an example hinge 112a of the kickstand 112 depicted in FIG. 2. In FIG. 3, a first hinge element 118a at a first end of the support 114 is coupled to the first hinge 112a. In FIG. 4, the first hinge element 118a is decoupled from the first hinge 112a. As shown in FIG. 4, the first hinge element 118a is coupled to or integrated with the first end of the support 114. Accordingly, the first hinge element 118a interfaces with the first hinge 112a by positioning (e.g., inserting) the first hinge element 118a within an opening 113 defined in the first hinge 112a. In this example, the opening 113 is substantially circular, with a cutout that forms two, substantially flattened portions 111a, 111b of the opening 113. The flattened portions 111a, 111b are intersecting and are oriented at an angle relative to each other. In other words, the cutout is V-shaped with two flattened portions 111a, 111b. In this example, the two flattened portions 111a, 111b are oriented at an obtuse angle to each other. Said another way, the two flattened portions 111a, 111b of the cutout form an obtuse angle. In this example, the first hinge element 118a is press fit into the opening 113 defined in the first hinge 112a.

The hinge element 118a (sometimes referred to herein as a "torque insert 118a") may include a shaft 121 and a housing 123 coupled to the shaft 121. The housing 123 is configured to rotate about (or around) the shaft 121. Friction between the shaft 121 and the housing 123 resists or constrains rotation of the housing 123 about the shaft 121. In this example, a number of torque elements (e.g., hardened steel elements) are disposed within of the hinge element 118a, and the amount of torque to overcome the frictional force between the shaft 121 and the housing 123 may be controlled by the number of torque elements within the hinge element 118a, as well as lubricant between the shaft 121 and the housing 123. Accordingly, the hinge element 118a may be rotatable with the application of torque at any suitable torque value, such as a torque value within a range of about 0.5 to 10 newton meters (N-M) (or 4.4 to 88.6 pound-inches (lb-in)). For example, the torque value of the hinge element 118a may be at least about 1 N-m (or 8.85 lb-in). Different hinge elements 118a with different torque values may be available to select a hinge element 118a with a desired torque value for the application. In some examples, the torque varies with the rotation of the shaft 121 within the housing 123 of the hinge element 128 to provide variable torque depending on how far the support 114 is rotated away from the medical device 102. For example, the torque may increase as the support 114 of the kickstand 110 is rotated farther from the medical device 102, making it gradually harder to move the kickstand 110 as the support 114 of the kickstand 110 is rotated farther from the medical device 102, or vice versa. In other examples, the torque is substantially constant throughout the full range of rotation. When the hinge element 118a is disposed within the opening 113, and as the housing 123 of the hinge element 118a rotates about the shaft 123, the friction between the components (121, 123) of the hinge element 118a inhibits, resists or constrains further rotation of the support 114 relative to the medical device 102. Accordingly, the hinge element 118a is configured to effectively "lock" or restrain the adjustable kickstand 110 in an extended position until a greater force (e.g., a force that exceeds the torque value associated with the hinge element 118a) is applied to the kickstand 110 to overcome this "locked" position of the kickstand 110.

For example, to collapse the adjustable kickstand 110, the user exerts a force on the adjustable kickstand 110 to overcome the force of friction between the components (121, 123) of the hinge element 118a to allow the rotation of the shaft 121 within the housing 123 of the hinge element 118a. The user can then continue moving the adjustable kickstand 110 until the kickstand 110 is moved to the collapsed position. With the adjustable kickstand 110 in the collapsed position.

The adjustable kickstand 110 is configured to be positioned at intermediate extended positions between the collapsed position and a maximum extended position. When the kickstand 110 is placed in one of the intermediate extended positions, the friction between components (121, 123) of the hinge element 118a is sufficient to prevent or inhibit rotation of the adjustable kickstand 110 when the medical device 102 is resting on a surface in a reclined orientation. That is, the user may rotate the kickstand 110 to any desired position, and rotation is limited by hinge element 118a. Thus, in some examples, the full range of rotation is between the collapsed position shown in FIG. 3 and a fully (or maximum) extended position. In other examples, the adjustable kickstand 110 is rotatable to one of multiple preset positions.

Other "locking" features may be used to inhibit rotation of the adjustable kickstand 110 from the collapsed position to an extended position, or vice versa. In an example, a releasable catch is automatically engaged to inhibit or prevent rotation of the adjustable kickstand 110 from the collapsed position, and/or from extended position. By inhibiting or preventing the rotation of the adjustable kickstand 110 from one or more of these positions, the adjustable kickstand 110 is prevented from unintentionally collapsing and/or from unintentionally extending.

In FIG. 3, the hinge element 118a is disposed within the opening 113 of the hinge 112a. The hinge 112a includes the opening 113 in which the hinge element 118a is inserted. The opening 113 is substantially circular and includes the cutout along one portion of the opening 113. In this example, the cutout is V-shaped with two flattened portions 111a and 111b that intersect each other and have an angle therebetween. As discussed previously, in this example, the angle between the two flattened portions 111a, 111b of the opening 113 is an obtuse angle.

FIG. 4 illustrates a detailed view of a first hinge element 118a. The first hinge element 118a is coupled to or integrated with a first end of the support 114 so that, as the support 114 is moved between the collapsed position and an extended position, the shaft 121 of the first hinge element 118a rotates as well. The first hinge element 118a is substantially circular and includes a flattened portion 119 in its exterior surface. In FIG. 4 splines are positioned about the exterior surface of the hinge element 118a. For example, the hinge element 118a is shaped as a cylinder with a substantially circular profile or cross-section, and the splines run lengthwise along the exterior surface of cylinder. The splines positioned about the exterior surface of the hinge element 118a are configured to contact the interior surface of the opening 113 of the hinge 112a, which may open into a cylindrical hole. The splines prevent the hinge element 118a from rotating the opening 113, which allows the shaft 121 of the hinge element 118a to rotate within the housing of the hinge element 118a. Alternatively, the exterior surface of the cylindrical hinge element 118a can be substantially smooth such that a majority of the exterior surface of the hinge element 118a contacts the interior surface of the opening 113. In any case, the friction between the exterior surface of the hinge element 118a and the interior surface of the opening 113 inhibits or resists rotation of the hinge element 118a within the opening 113, and the friction between the shaft 121 and the housing 123 of the hinge element 118a allows the adjustable kickstand 110 to be restrained at any orientation between the collapsed position and the maximum extended position. To further increase the friction between the hinge element 118a and the interior surface of the opening 113, one or both can be constructed of or include a coating that is a relatively high friction material (e.g., rubber) to help restrain or inhibit rotation of the hinge element 118a within the opening 113a. In another alternative, the geometry or dimensions of the splines defined in the exterior surface of the hinge element 118a are adjustable to increase or decrease the amount of surface area of the hinge element 118a that is in contact with the interior surface of the opening 113, thereby modifying the amount of friction between the two elements to inhibit the rotation of the hinge element 118a within the opening 113.

Figure 5:
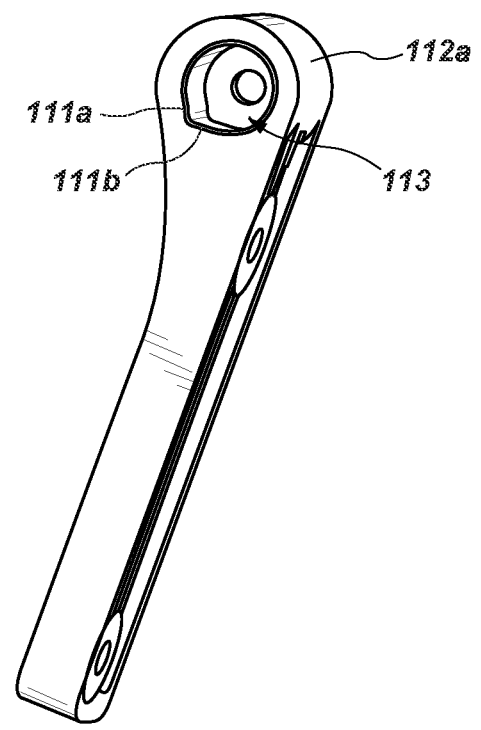
FIG. 5 illustrates a side perspective view of an example hinge of the kickstand depicted in FIG. 2.

FIG. 5 illustrates a side perspective view of the first hinge 112a. It is to be appreciated that the second hinge 112b is a mirrored version of first hinge 112a, and, hence, the description of the first hinge 112a applies to the second hinge 112b, except that some aspects may be in reverse. In this example, the first hinge 112a is substantially a plate with a protruding and rounded portion at an upper end of the hinge 112a. The flat, plate-like lower portion of the hinge 112a includes openings that are configured receive fasteners to couple the hinge 112a to the medical device 102. The protruding, rounded portion of the hinge 112a includes the opening 113 that extends horizontally through the hinge 112a to form a cavity (e.g., a cylindrical hole) within which the hinge element 118a is inserted (e.g., press fit). In some examples, the cavity defined in the hinge 112a includes a back wall that restrains the hinge element 118a at the end of the cavity. In some examples, the end of the cavity includes another opening that is smaller than the opening 113 and that allows the shaft 121 of the hinge element 118a to pass therethrough to couple to an end of the support 114. Like the hinges 112a, 112b, the ends of the support 114 are mirrored as well, meaning that the description of the first hinge element 118a applies to the second hinge element at the second, opposite end of the support 114.

Figure 6A:
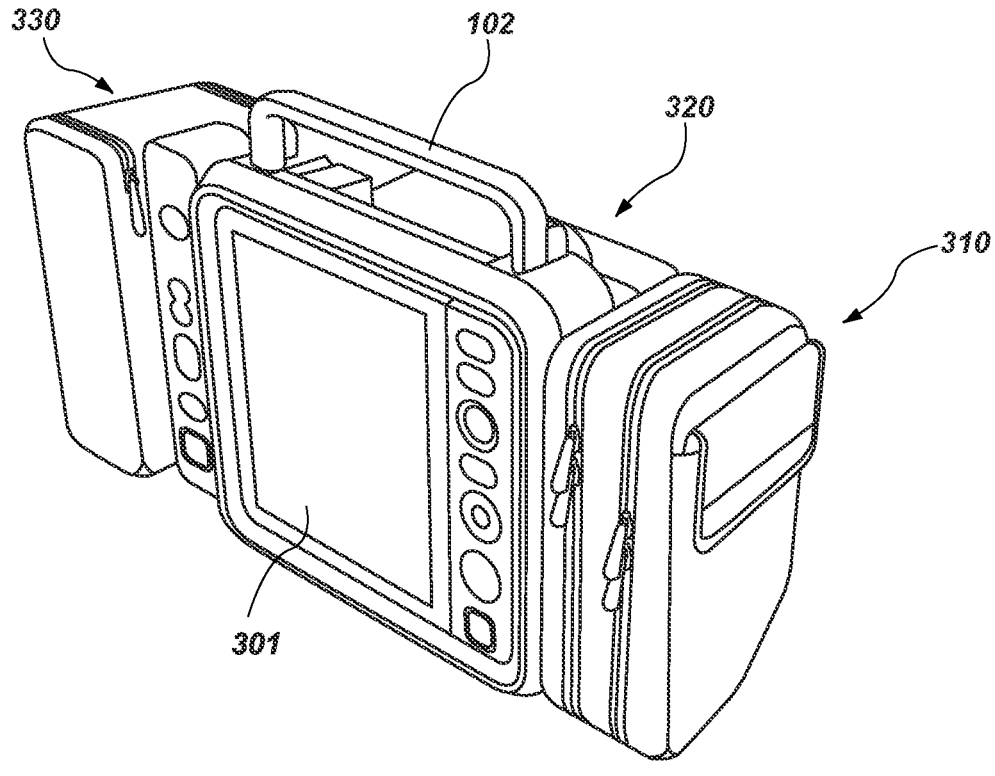
FIG. 6A illustrates a front perspective view of an example medical device having example storage bags coupled thereto.
Figure 6B:
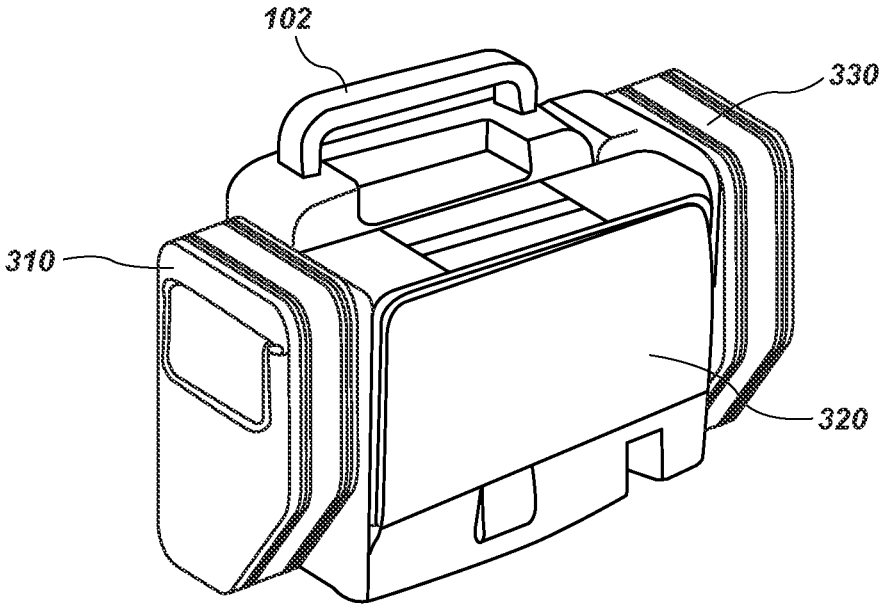
FIG. 6B illustrates a rear perspective view of the medical device and storage bags depicted in FIG. 6A.

FIGS. 6A and 6B illustrate example external storage bags 310, 320, 330 that are configured to be coupled to the medical device 102. In this example, a surface of individual ones of the storage bags 310, 320, 330 that faces or contacts the medical device 102 includes hardware, such as one or more clips that engage a portion of, or hardware on, the exterior surface of the medical device 102 in order to couple the storage bags 310, 320, 330 thereto. In another example, the storage bags 310, 320, 330 are configured to be coupled or fastened to the exterior of the medical device 102, such as by screws or other releasable fastener. In some examples, the coupling between the storage bags 310, 320, 330 and the medical device 102 is selectively releasable to secure the storage bags 310, 320, 330 to the medical device 102 while allowing a user to remove the storage bags 310, 320, 330 from the medical device 102 when desired. That is, the storage bags 310, 320, 330, in some examples, are configured to be decoupled from the medical device 102 to allow the medical device 102 to be transported by itself.

In this example, the storage bags 310, 320, 330 are configured to carry or otherwise store various medical device 102 accessories, such as sensors, electrodes, a printer, and/or other items a user may wish to carry with the medical device 102. Internal organizers, such as folders, shelves, dividers, pockets, and/or other organizers, can be included in the storage bags 310, 320, 330, and/or external pockets or organizers can be included on the storage bags 310, 320, 330. This organization capability allows the user to efficiently and accurately access or retrieve accessories, which helps reduce delays in the treatment and/or monitoring of a patient using the medical device 102. In some examples, external doors, covers, or flaps are usable to access the internal compartment(s) of the storage bags 310, 320, 330, and the external doors, covers, or flaps include fasteners, such as hook-and-loop fasteners, magnetic closures, zippers, and/or other fasteners, to securely close the external doors, covers, or flaps to enclose the contents within the storage bags 310, 320, 330. In other words, the storage bags 310, 320, 330 are openable and closable, such as by zipping a zipper to open or close the storage bags 310, 320, 330. The storage bags 310, 320, 330 can be configured to be selectively coupled to the medical device 102, allowing the storage bags 310, 320, 330 to be coupled to, and moved with, the medical device 102, or decoupled, and moved separately, from the medical device 102. This provides a versatile medical device 102 with storage bags 310, 320, 330 for aiding in the transport and organization of various accessories that are usable with the medical device 102. In some examples, the storage bags 310, 320, 330 include various openings that allow cables or connections from the medical device 102 to be coupled to various systems or devices, such as medical device 102 accessories, that are contained or carried within the bags 310, 320, 330, even when the storage bags 310, 320, 330 are closed. In this manner, the medical device 102 accessories carried within the storage bags 310, 320, 330 can remain coupled to the medical device 102 and ready for use by a user to reduce delays in patient monitoring and/or treatment.

The storage bags 310, 320, 330 can be soft-sided, with a foam construction that includes an outer covering that is soft, durable and substantially non-abrasive, such as a fabric or woven material. The outer covering of the storage bags 310, 320, 330 can include antimicrobial properties, and/or the outer covering can be cleanable to allow the storage bags 310, 320, 330 to be cleaned and disinfected, as desired. The ability to clean or disinfect the storage bags 310, 320, 330 prevents contamination between patients or treatment environments. The soft-sided nature of the storage bags 310, 320, 330 provides cushioning and protection for the contents within the storage bags 310, 320, 330 and prevents or minimizes damage caused by the storage bags 310, 320, 330 contacting a person or objects. The exterior walls of the storage bags 310, 320, 330 can include formed, rigid plastic sheets, frames, inserts or shells to provide structure, shape and support for the storage bags 310, 320, 330, and to make the exteriors of the storage bags 310, 320, 330 semi-rigid. Additionally, rigid material within the exteriors of the storage bags 310, 320, 330 allows hardware to be coupled to the exterior of the bags 310, 320, 330, such as hardware (e.g., clips or other fasteners) that is used to couple the storage bags 310, 320, 330 to the medical device 102. The semi-rigid walls of the storage bags 310, 320, 330 also provide structure and support for the internal organizers or compartments of the storage bags 310, 320, 330. The side panels of the storage bags 310, 320, 330, such as side storage bags 310, 330, can include slots to accommodate flat sheets of material to form shelves within the side storage bags 310, 330. Alternatively, various supports for the shelves are mounted to the side panels of the side storage bags 310, 330 to support the installation of the shelves within the side storage bags 310, 330.

In the example of FIGS. 6A and 6B, the side storage bags 310, 330 contain accessories (e.g., sensors, etc.) for use with the medical device 102, and other resources for a user of the medical device 102. In some examples, the rear storage bag 320 contains a printer that is configured to be connected to the medical device 102 via a printer port to print various readouts or other information, such as electrocardiogram (ECG) printouts. In these examples, the user of the medical device 102 is able to carry the medical device 102 and the storage bags 310, 320, 330 as a self-contained unit that contains various resources the user may need for monitoring and/or treating a patient.

Figure 7:
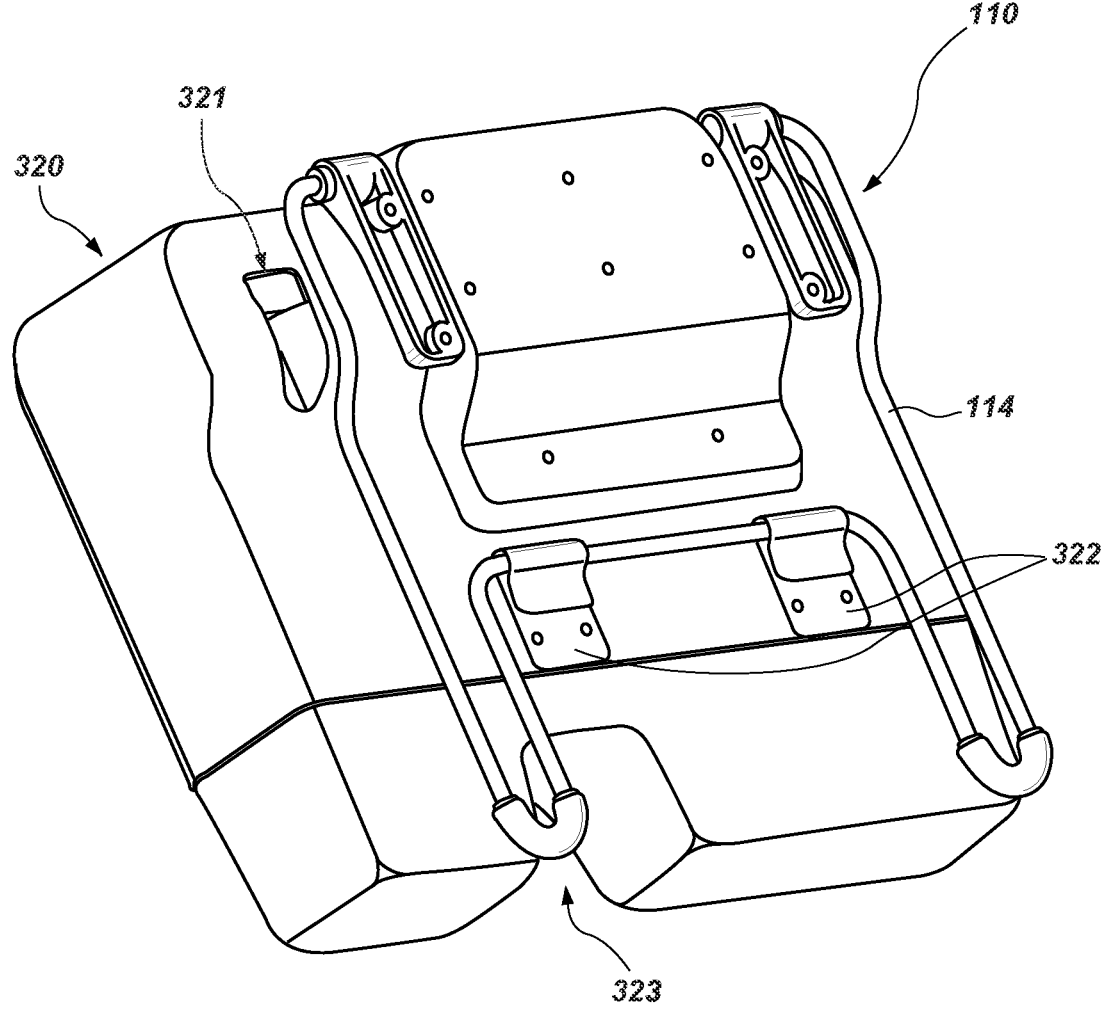
FIG. 7 illustrates a rear perspective view of an example rear storage bag coupled to the kickstand depicted in FIG. 2.

FIG. 7 illustrates a rear perspective view of the rear storage bag 320. The rear storage bag can e.g. be a printer bag configured to store, contain, or carry a printer. FIG. 7 illustrates the rear storage bag 320 coupled to the kickstand 110 described above, thereby illustrating how the rear storage bag 320 is configured to be coupled to the medical device 102 (not shown in FIG. 7). The rear of the rear storage bag 320, which is the side of the rear storage bag 320 adjacent to (and facing) the medical device 102, includes clips 322 that clip onto (or slide over) a portion of the support 114 (e.g., a horizontal crossbar of the support 114) of the kickstand 110 to couple the rear storage bag 320 to the medical device 102. The use of the clips 322 disposed on the exterior surface of the rear storage bag 320 allows the rear storage bag 320 to easily and quickly couple to the kickstand 110 of the medical device 102. Similar hardware may be disposed on the exterior surface of the side storage bags 310, 330 to removably couple those storage bags 310, 330 to the sides of the medical device 102, which may have corresponding hardware, such as a horizontal bar. In this example, the rear storage bag 320 also includes a notch 323 defined in the base (e.g., along the lower portion) of the rear storage bag 320. The notch 323 allows access to the power connector 104 disposed on the back of the medical device 102 in the lower right quadrant of the back of the medical device 102 (See FIG. 1A). This allows medical device 102 to be placed into a docking station or coupled to a power cable while the rear storage bag 320 is coupled to the rear of the medical device 102, because the rear storage bag 320 does not obstruct the power connector 104 when it is coupled to the medical device 102. The rear of the rear storage bag 320 also includes an opening 321 to allow a device, such as a printer to be coupled to a port, such as a printer port, of the medical device 102, such as via a wired connection between the device (e.g., printer) and the medical device 102. In the example of the printer, the printer is external to the medical device 102, and the connection between the medical device 102 and the printer is made via the opening 321 defined in the rear storage bag 320 (e.g., printer bag) while the printer is stored within the interior of the rear storage bag 320 (e.g., printer bag) and while the rear storage bag 320 (e.g., printer bag) is closed.

The rear storage bag 320 (e.g., printer bag) locates the stored device, such as the printer (stored within the rear storage bag 320) external to the medical device 102. Some conventional systems permanently integrate a printer with a medical device, which increases the bulk of the medical device and printer system. Moreover, modern communications and display technology allows ECG waveforms to be viewed digitally on external devices in communication with the medical device 102 and/or on the display 301 of the medical device 102 itself, and the user is able to manipulate the ECG signal or take various measurements based on the digital output on the display 301. The reduced reliance on a physical printout means the printer can be separated from the medical device 102 and used as an optional accessory to the medical device 102, thereby reducing the bulk and size of the medical device 102. An external printer is configured to be coupled to the medical device 102 (e.g., via a wired connection), and the rear storage bag 320 (e.g., printer bag) provides an efficient mechanism to carry and/or store a device (e.g., the printer) for use in conjunction with the medical device 102.

Figure 8A:
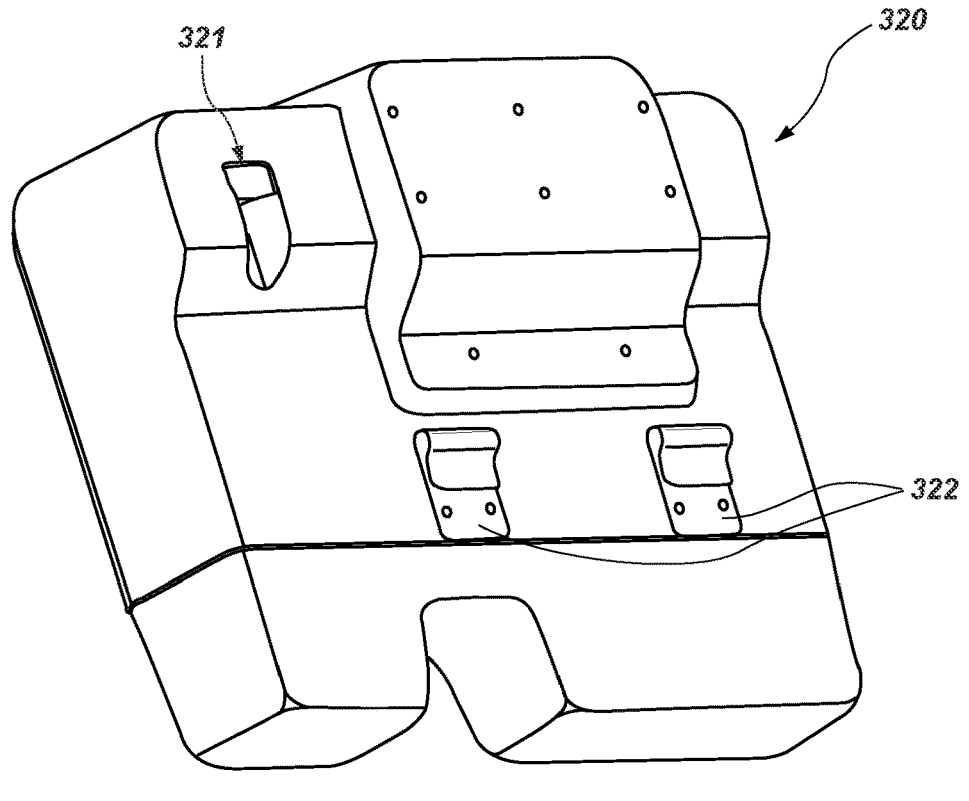
FIG. 8A illustrates another rear perspective view of the example rear storage bag depicted in FIG. 7 without a kickstand coupled thereto.
Figure 8B:
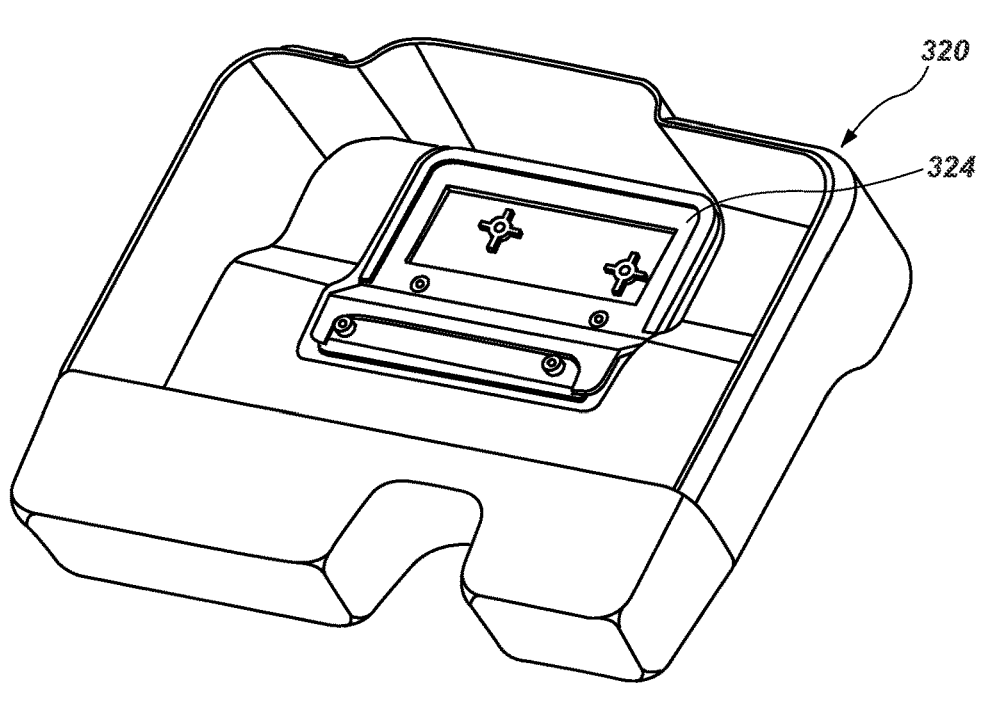
FIG. 8B illustrates a front perspective view of the example rear storage bag depicted FIG. 7.

FIG. 8A illustrates another rear perspective view of the example rear storage bag 320 depicted in FIG. 7, but without a kickstand coupled thereto. In FIG. 8A, the clips 322 are not coupled to a crossbar of the support 114 of the kickstand 110 so that more of the clips 322 on the exterior surface of the rear storage bag 320 are visible in FIG. 8A. FIG. 8B illustrates a front perspective view of the rear storage bag 320, showing an interior of the rear storage bag 320 with an outer covering not shown in FIG. 8B. In this example, the interior of the rear storage bag 320 includes a rigid plastic insert 324 that is an interface to which a device, such as the printer (not shown in FIG. 8B), is mountable. In this example, a device, such as the printer, is configured to be coupled to the plastic insert 324 using various fasteners, and a connection from the device (e.g., the printer) to the medical device 102 is configured to be routed through the opening 321 depicted in FIG. 7 and FIG. 8A, which allows the device (e.g., the printer) to be coupled to a port (e.g., a printer port) disposed on an exterior surface of the medical device 102 while the device (e.g., the printer) is stored in the interior of the rear storage bag 320 (e.g., printer bag) and while the rear storage bag 320 (e.g., printer bag) is closed.

Figure 9A:
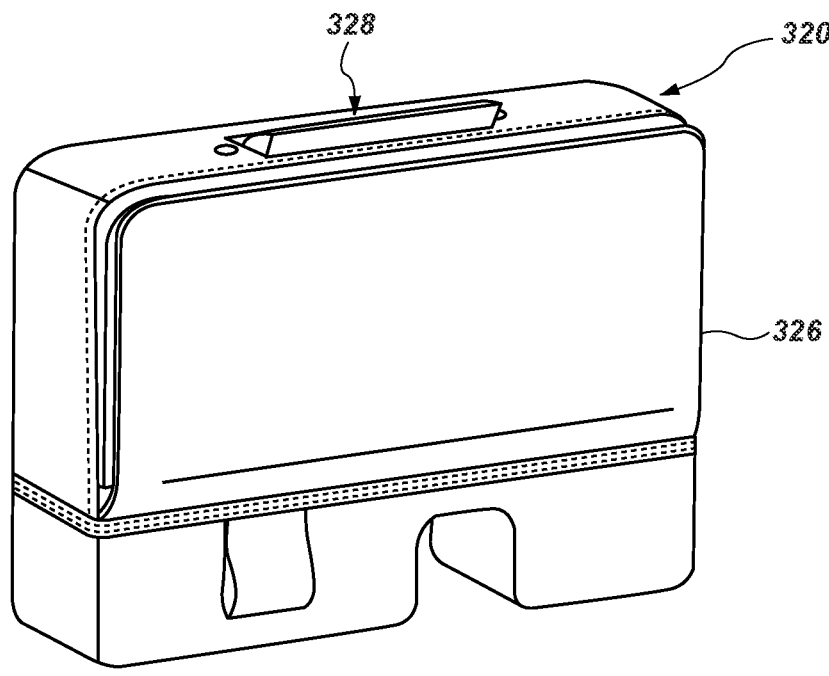
FIG. 9A illustrates another front perspective view of the example rear storage bag depicted in FIG. 7 when the rear storage bag is closed.
Figure 9B:
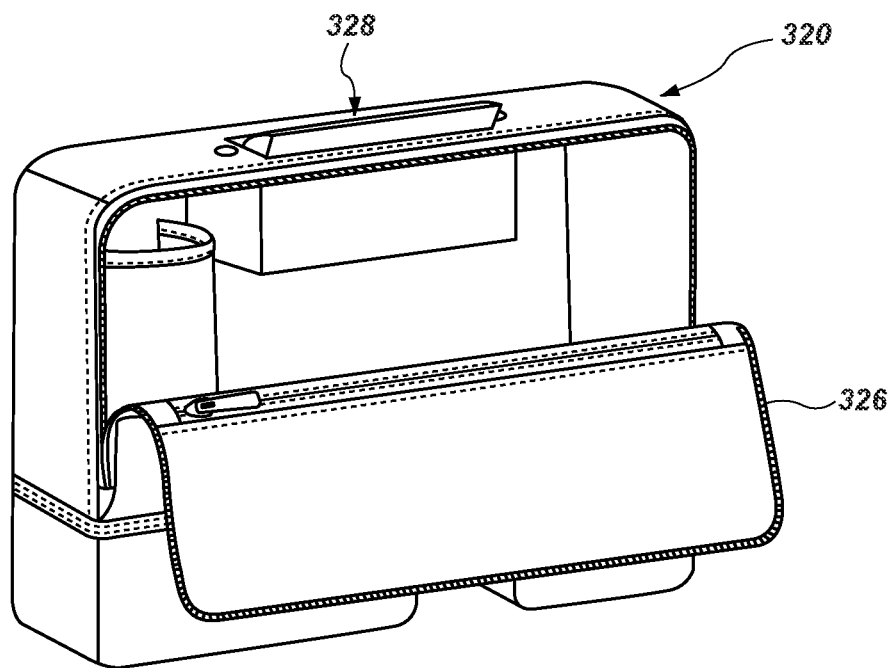
FIG. 9B illustrates the front perspective view of the example rear storage bag depicted in FIG. 7 when the rear storage bag is opened.

FIGS. 9A and 9B illustrate front perspective views of the rear storage bag 320 with the outer covering 326 shown. The outer covering 326 is closed in FIG. 9A to close the rear storage bag 320, and opened in FIG. 9B to open the rear storage bag 320. In this example, the outer covering 326 includes a zipper or other closure mechanism (e.g., snaps, hook-and-loop fasteners (e.g., Velcro®), latches, magnets, etc.) to selective close the outer covering 326 by securing the outer covering 326 to a remainder of the rear storage bag 320. A user can unzip or otherwise open the outer covering 326 to access the interior of the rear storage bag 320. The interior of the rear storage bag 320 can include organizers, such as pockets, dividers, shelves, and/or other organizers to contain and/or organize resources or other contents within the rear storage bag 320. In an example, the outer covering 326 includes an inner pocket to store items within the rear storage bag 320, which may enclose the items when the outer covering 326 is closed. In this example, the rear storage bag 320 (e.g., printer bag) includes a printout opening 328 at the top of the rear storage bag 320 (e.g., printer bag). In these examples, printouts from the printer are configured to be directed or routed through the printout opening 328 to allow a user to access or retrieve the printout.

Figure 10A:
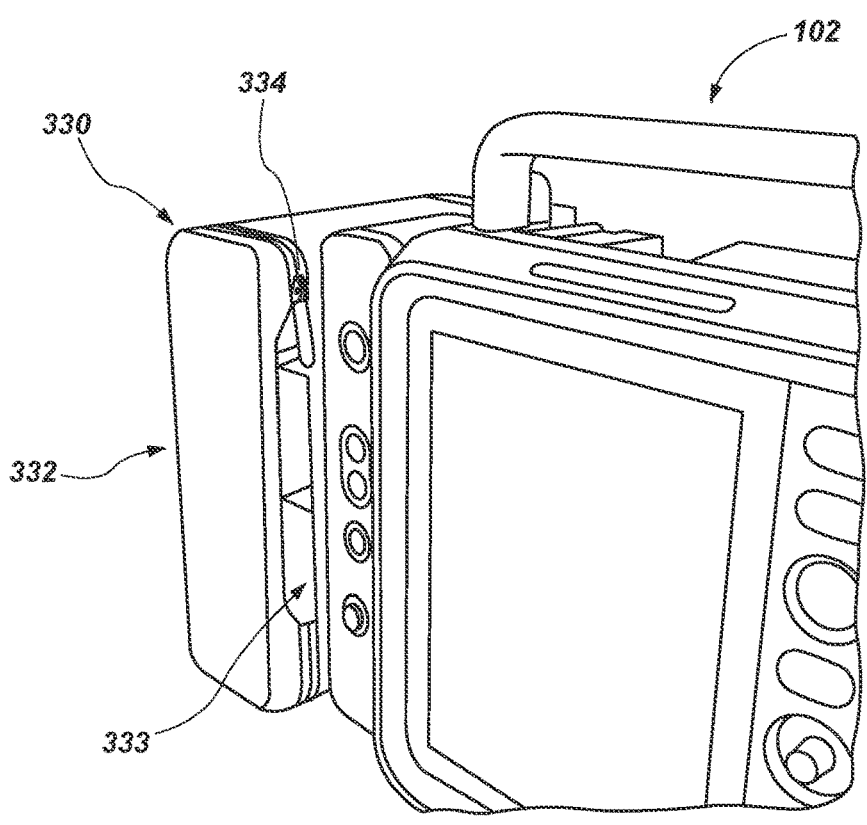
FIG. 10A illustrates a front perspective view of an example left side storage bag coupled to an example medical device with a front cover of the storage bag closed.
Figure 10B:
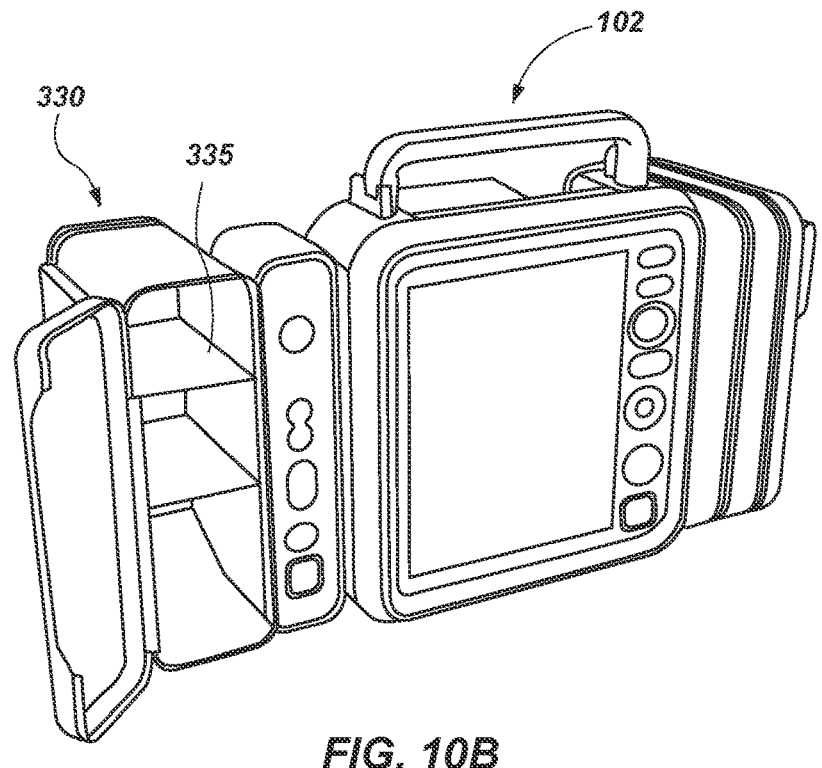
FIG. 10B illustrates another front perspective view of the left side storage bag depicted in FIG. 10A with the front cover of the storage bag opened.
Figure 10C:
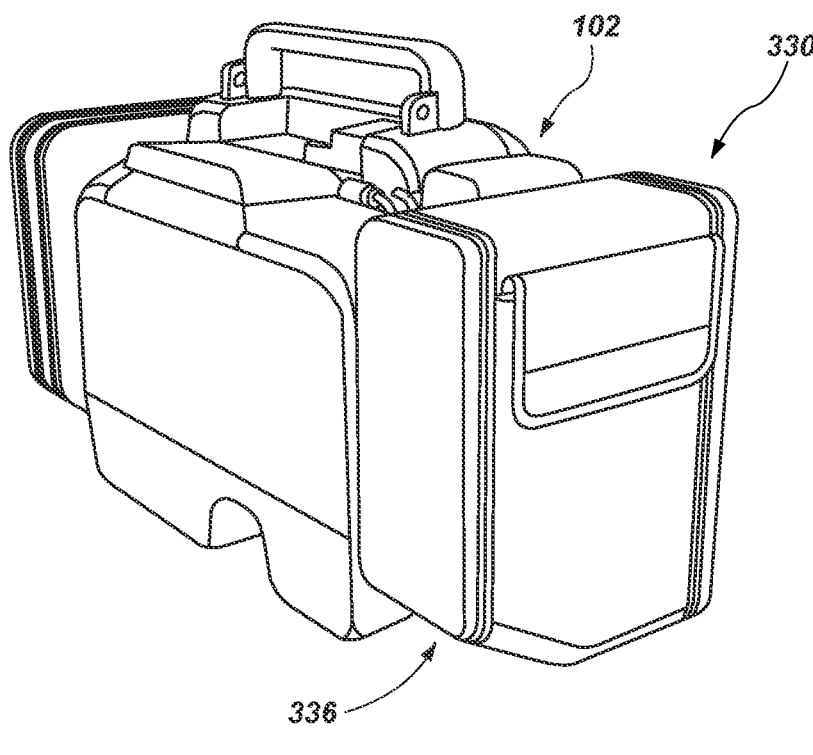
FIG. 10C illustrates a rear perspective view of the left side storage bag depicted in FIG. 10A with a rear cover closed.
Figure 10D:
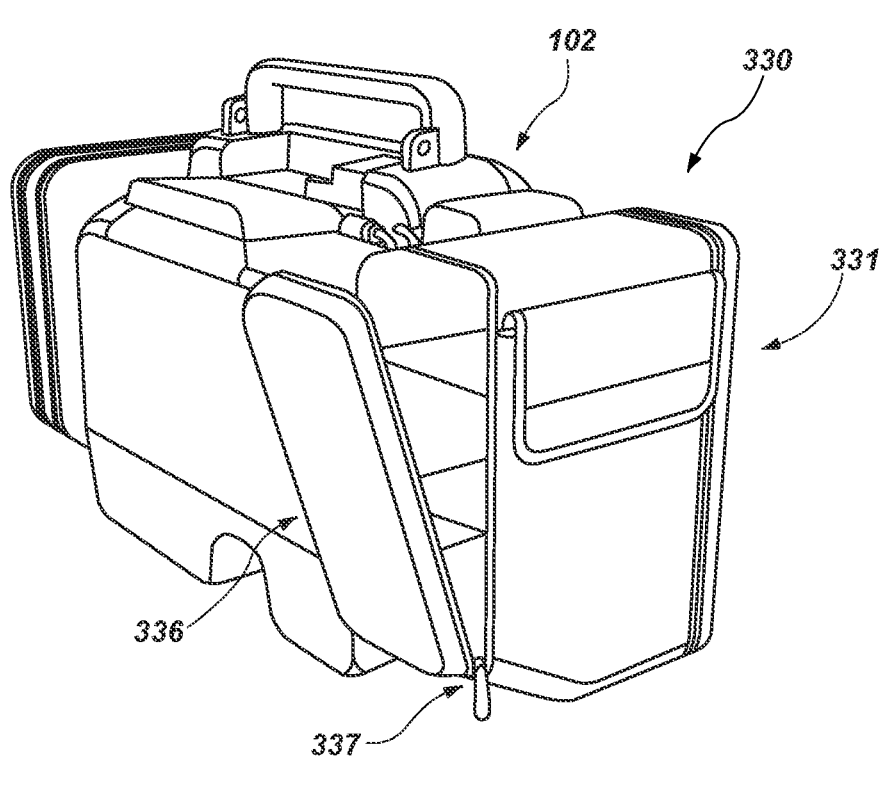
FIG. 10D illustrates the rear perspective view of the left side storage bag depicted in FIG. 10A with the rear cover opened.

FIGS. 10A-10D illustrate various views of a medical device 102 with a storage bag (e.g., a left side storage bag 330) coupled thereto. As shown in FIG. 10D, the left side storage bag 330 has a side pocket 331 that includes a flap to cover the opening of the pocket 331. The flap of the side pocket 331 has a closure mechanism, such as a hook-and-loop or magnetic fastener, to secure the flap in the closed position. As shown in FIGS. 10A and 10B, a front cover 332 of the left side storage bag 330 covers shelves 335 within the interior of the left side storage bag 330. The front cover 332 is shown in FIG. 10A as being flat on a front surface thereof. In some examples, the front cover 332 bulges outward in a region of the front cover 332, such as at the bottom region of the front cover 332, to accommodate accessories that are bulky. Various accessories for use with the medical device 102 are storable on the shelves 335 of the left side storage bag 330, and cables or cords from the various accessories are configured to pass through a cutout 333 (sometimes referred to herein as an "opening 333") defined in the front cover 332, which allows for coupling accessories stored within the left side storage bag 330 to the medical device 102, which can remain coupled while storage bag 330 is closed (e.g., while the front cover 332 is closed by a zipper 334). By allowing the accessories to remain coupled to the medical device 102 when the medical device 102 is not in use, the accessories are more readily and quickly accessible to a user of the medical device 102, thereby reducing delays in patient monitoring and/or treatment using the medical device 102.

The pre-connected cables or cords from the various accessories are configured to be placed in any storage bag 310, 320, 330. In this example, they are described as being contained within the left side storage bag 330, but accessories can additionally, or alternatively, be included in a right side storage bag(s) 310 or elsewhere to accommodate the connection of accessory cables to nearby ports on the medical device 102. The pre-connected cable or cord openings in the bags 310, 320, 330 can be matched to or aligned with the ports on the exterior surface of the medical device 102 and available for the various cables and cords of the medical device 102. The port location may vary by device design; and, therefore, the location of the pre-connected cable or cord openings in the bags 310, 320, 330 may likewise vary by device design.

As shown in FIGS. 10C and 10D, the rear of the left side storage bag 330 has an openable portion 336 (e.g., sometimes referred to herein as a "rear cover 336") that is secured to the left side storage bag 330 by a zipper 337. By unzipping the zipper 337, the rear cover 336 is configured to be tilted or moved away from the rear of the left side storage bag 330. In other examples, the rear of the left side storage bag 330 is not openable and does not include the zipper 337. The rear cover 336 can include hardware, such as a clip, that is configured to be used to store a modem (e.g., a cellular modem) or data communication device that the medical device 102 is configured to use to send and receive data. The modem or data communication device is configured to be placed into a cradle or holder that can be configured to be coupled to the hardware in the rear cover 336 to securely store the modem or data communication device within the left side storage bag 310. A connection between the modem or data communication device and the medical device 102 can be a wired connection that passes through the left side storage bag 330 to the medical device 102. Alternatively, the connection between the medical device 102 and the modem or data communication device is a short-range wireless connection and the modem or data communication device is configured to transmit data to and/or receive data from an external device or system by a different wireless connection.

FIGS. 11A-11D illustrate various views of a right side storage bag 310 coupled to the medical device 102. In this example, the right side storage bag 310 has a side pocket 311 that includes a flap to cover the opening of the pocket 311. The flap of the pocket 311 can have a closure mechanism, such as a hook-and-loop or magnetic fastener, to secure the flap in the closed position. In this example, two zippers 312 and 315 are included on the right side storage bag 310 to open and close the right side storage bag 310, thereby allowing the user to selectively access a first interior portion 313 and a second interior portion 316 of the right side storage bag 310. In an example, the first interior portion 313 (shown in FIG. 11B) is configured to include or store accessories for treating a patient, such as various therapy electrodes, and the second interior portion 316 (shown in FIG. 11C) is configured to include or store accessories for monitoring a patient, such as ECG electrodes or sensors. The two interior portions 313, 316 of the right side storage bag 310 can include color themes or coding to assist a user with quickly, visually distinguishing or identifying one of the interior portions 313, 316 from the other and associating a respective one of the interior portions 313, 316 with a specific function of treating or monitoring a patient.

Figure 11A:
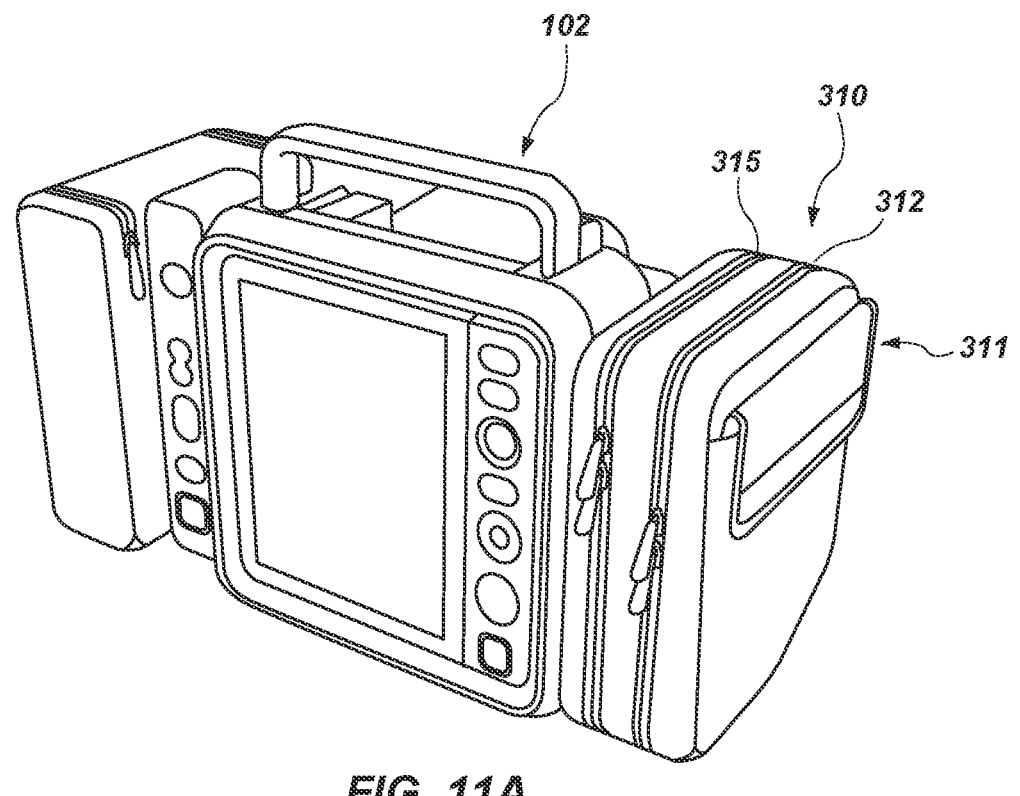
FIG. 11A illustrates a front perspective view of an example right side storage bag coupled to an example medical device.
Figure 11B:
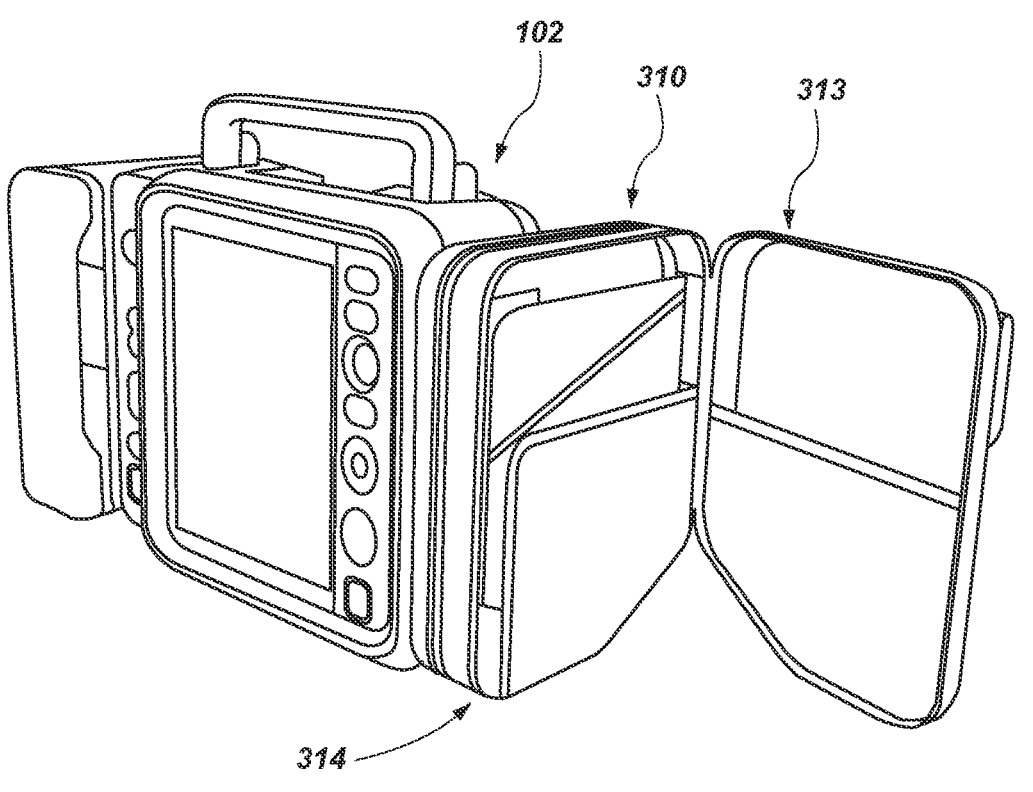
FIG. 11B illustrates a front perspective view of a first interior of the right side storage bag depicted in FIG. 11A.
Figure 11C:
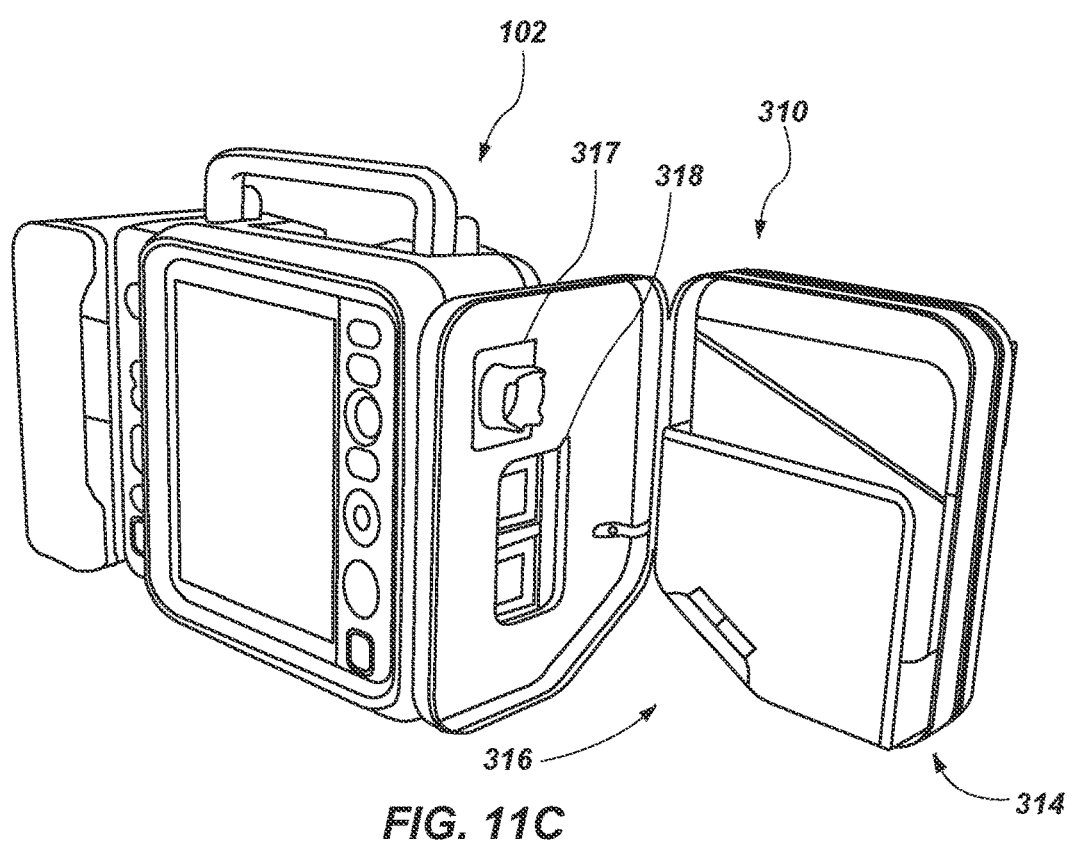
FIG. 11C illustrates another front perspective view of a second interior of the right side storage bag depicted in FIG. 11A.
Figure 11D:
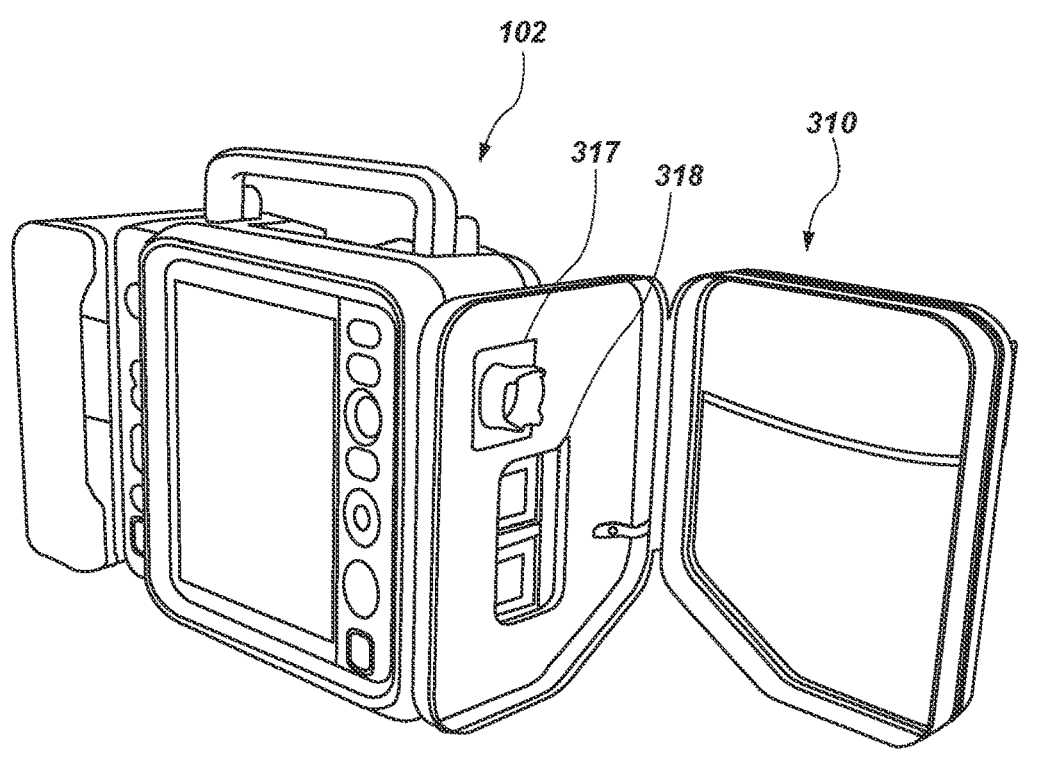
FIG. 11D illustrates yet another front perspective view of the interior of the right side storage bag depicted in FIG. 11A with a divider between the first interior and the second interior of the right side storage bag removed from the storage bag.

In this example, the first interior portion 313 of the right side storage bag 310 includes pockets or dividers for storing various accessories, such as packages of disposable electrodes. The disposable electrodes can be configured to be connected to the medical device 102 while the electrodes are stored within the first portion 313 of the right side storage bag 310 and while the storage bag 310 is closed (e.g., by zipping shut at least the zipper 312) to reduce the time to patient treatment and/or monitoring using the disposable electrodes. The disposable electrodes can include a portion of an electrode cable that extends from the electrode's packaging, and the electrode cable is configured to be connected to a therapy cable that is connected, or is connectable, to a defibrillation port on an exterior surface of the medical device 102 to reduce the time needed to configure the medical device 102 for treating and/or monitoring the patient. In this example, a divider 314 is configured to be positioned within the interior of the right side storage bag 310 to divide the two interior portions 313 and 316. In this example, the divider 314 is removable from the interior of the right side storage bag 310, such as shown in FIG. 11D, and the divider 314 is configured to be secured within the interior of the right side storage bag 310 using one or more fasteners, such as snaps. When the divider 314 is removed, the user has access to both the first and second interior portions 313, 316 of the right side storage bag 310 when one of the zippers 312, 315 is unzipped.

In this example, the second interior portion 316 of the right side storage bag 310 includes pockets or dividers, such as the divider 314, for storing various accessories. In an example, the stored accessories include accessories for monitoring a patient, such as ECG electrodes, or other monitoring accessories or systems. As shown in FIG. 11C, the second interior portion 316 can also contain cutouts 317, 318 (sometimes referred to herein as "openings 317, 318") to allow a user to access portions of the medical device 102 through the interior of the right side storage bag 310. In this example, the opening 317 is configured to accommodate an ECG port guard 200 coupled to the medical device 102, allowing the user to access the ECG port 202 of the medical device 102. In the example, the user can retrieve an ECG sensor and electrodes from the divider 314, place the electrodes on the patient and couple the ECG sensor to the electrodes on the patient and to the medical device 102 via the ECG port 202 of the medical device 102 that is aligned with the opening 317 and thereby exposed within the interior of the right side storage bag 310. That is, the ECG port 202 of the medical device 102 is accessible via the opening 317, and a connector of the ECG sensor can be guarded by the ECG port guard 200 that is disposed within the opening 317 and extends into the interior of the storage bag 310. The ECG sensor can be configured to be coupled to the ECG port 202 of the medical device 102 while the ECG sensor is stored within the right side storage bag 310 and, in some cases, while the storage bag 310 is closed. The pre-connection of the ECG sensor reduces the time spent configuring the ECG sensor to begin monitoring the patient. In this example, the cutout 318 provides a user with access to the battery receptacles of the medical device 102. This cutout 318 allows the user to access the batteries for various purposes, such as to replace a battery. By providing such access through the cutouts 317, 318 of the second portion 316 of the interior of the right side storage bag 310, the right side storage bag 310 is not required to be removed for the user to have access to one or more ports or receptacles of the medical device 102.

FIGS. 13A-13H illustrate various views of the example right side storage bag 310 showing various features of the right side storage bag 310. The example right side storage bag 310 is configured to be coupled to a medical device, such as the medical device 102 described herein. In some examples, the example right side storage bag 310 includes openings or cutouts 317, 318 to allow cables and/or portions of the medical device 102 to extend through the right side storage bag 310 to an interior portion thereof, such as the second portion 316 of the interior of the right side bag 310, or to allow access to ports and/or other compartments of the medical device 102.

In medical emergencies, time is a critical factor in positive patient outcomes. By making the medical device accessories readily accessible and readily usable in an efficient manner, the storage bags 310, 320, 330 reduce the time to start patient monitoring and/or treatment. Reducing this critical time improves the patient treatment and monitoring to achieve better patient outcomes.

FIGS. 1A-1E and 12 illustrate an example port guard 200, such as an electrocardiogram (ECG) port guard 200. The port guard 200 is a guard element that is positioned about a port 202, such as an ECG port 202 of the medical device 102. The port 202 is sometimes referred to herein as an "accessory cable port." The port guard 200 is sometimes referred to herein as a "port collar." The port guard 200 protrudes from the exterior surface of the housing of the medical device 102 to protect a connection between a connector of a cable 201, such as an ECG cable 201 depicted in FIG. 1C, and the medical device 102. The cable 201 is sometimes referred to herein as an "accessory cable." The connector of the ECG cable 201 and the ECG cable 201 are connected at an attachment point. The ECG cable 201 is configured to be connected to the medical device 102, such as at the ECG port 202 of the medical device 102, at one end of the ECG cable 201. This electrically couples the ECG cable 201 to the various electrical components of the medical device 102 to treat or monitor the patient. The ECG cable 201 has ECG leads that are coupled to the patient on the other end of the ECG cable 201. The port guard 200 extends a distance beyond the attachment point between the connector of the ECG cable 201 and the ECG cable 201 when the connector of the cable is connected to the port, such as the ECG port 202. When an ECG cable connector is coupled to the medical device 102 via an ECG port 202, physical disruption of the connection between the ECG cable connector and ECG port 202, such as disconnection of the ECG cable 201, hinders or delays ECG signal acquisition and analysis by the medical device 102. For example, movement of the medical device 102 may cause the ECG cable connector to be dislodged or disconnected from the ECG port 202. Such movement of the medical device 102 may be caused by objects within the same environment as the medical device 102 contacting the ECG cable connector. Such disconnections further delay the patient monitoring and treatment because a user needs to spend time to reconnect the cable 201, and/or because the medical device 102 spends additional time to collect patient data after reconnection to resume its monitoring or treatment capabilities. Delays in ECG signal acquisition and analysis delay treatment decisions by the medical device 102 based on the ECG signal. These delays cause errors or delays in patient treatment or monitoring, which cause lower-quality patient outcomes. By protecting the ECG cable connection from physical disruption, the port guard 200 reduces the likelihood of a disconnection of the ECG cable 201 from the ECG port 202 of the medical device 102.

In an example, the medical device 102 represents a defibrillator that relies on an ECG signal that is received using an ECG cable 201 coupled to sensors placed on the patient. The medical device 102 is configured to monitor and/or treat the patient based on the ECG signal(s) received via the ECG cable 201. For example, a defibrillator analyzes the patient ECG signal to diagnose and make treatment recommendations or automatically initiate life-saving treatment, such as defibrillation therapy. Emergency rescuers often treat patients in a dynamic environment with several team members that are moving quickly to help administer lifesaving diagnostic and treatment to the patient. When the rescue team stabilizes the patient for transport, the medical device 102 is often transported with the patient for continued monitoring and treatment of the patient during transport. This high activity environment and the transport frequently results in the medical device 102 being accidentally bumped or dropped against hard objects, such as railings, the ground, vehicles, etc.

The port guard 200 is coupled, or is configured to be coupled, to the medical device 102 to retain the port guard 200 to the medical device 102, and the port guard 200 is positioned about a port, such as the ECG port 202, disposed on an exterior surface of the medical device 102, such as shown in FIGS. 1A-1E. The port guard 200 can be permanently, semi-permanently, or releasably coupled to the medical device 102, such as by an adhesive and/or a fastener(s). A distal portion 220 (sometimes referred to herein as the "outer portion 220") of the port guard 200 extends a distance from the exterior surface of the medical device 102 so that a connector coupled to a port, such as the ECG port 202, of the medical device 102 is shielded from contact to prevent dislodging or disconnecting the connector from the ECG port 202. As shown in FIG. 1C, the ECG cable 201 extends from the port guard 200, but the connector coupled to the ECG port 202 is shielded by the port guard 200 from contact with objects in the external environment. The shielding of the connector by the port guard 200 prevents or at least mitigates the disconnection of the ECG cable 201 from the ECG port 202. In some examples, the port guard 200 at least partially surrounds the ECG port 202 and protrudes from the exterior surface of the medical device 102 to help prevent the ECG cable 201 from disconnecting from the port 202.

Figure 12:
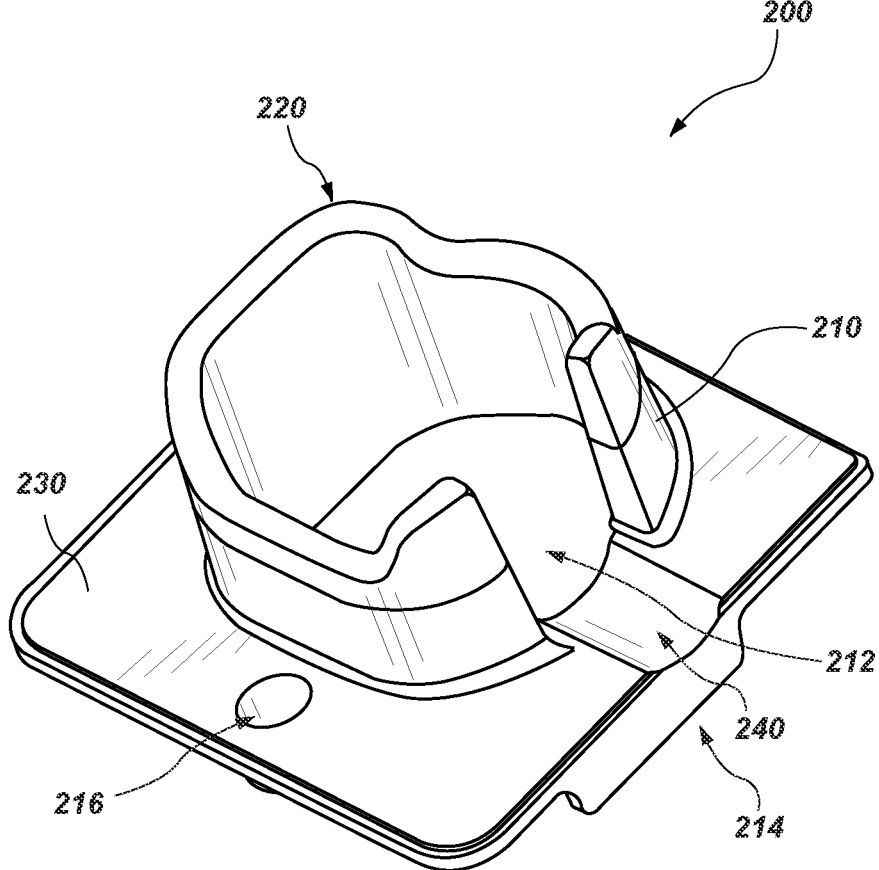
FIG. 12 illustrates an example port guard.
Figures 13E, 13F, 13G, 13H:
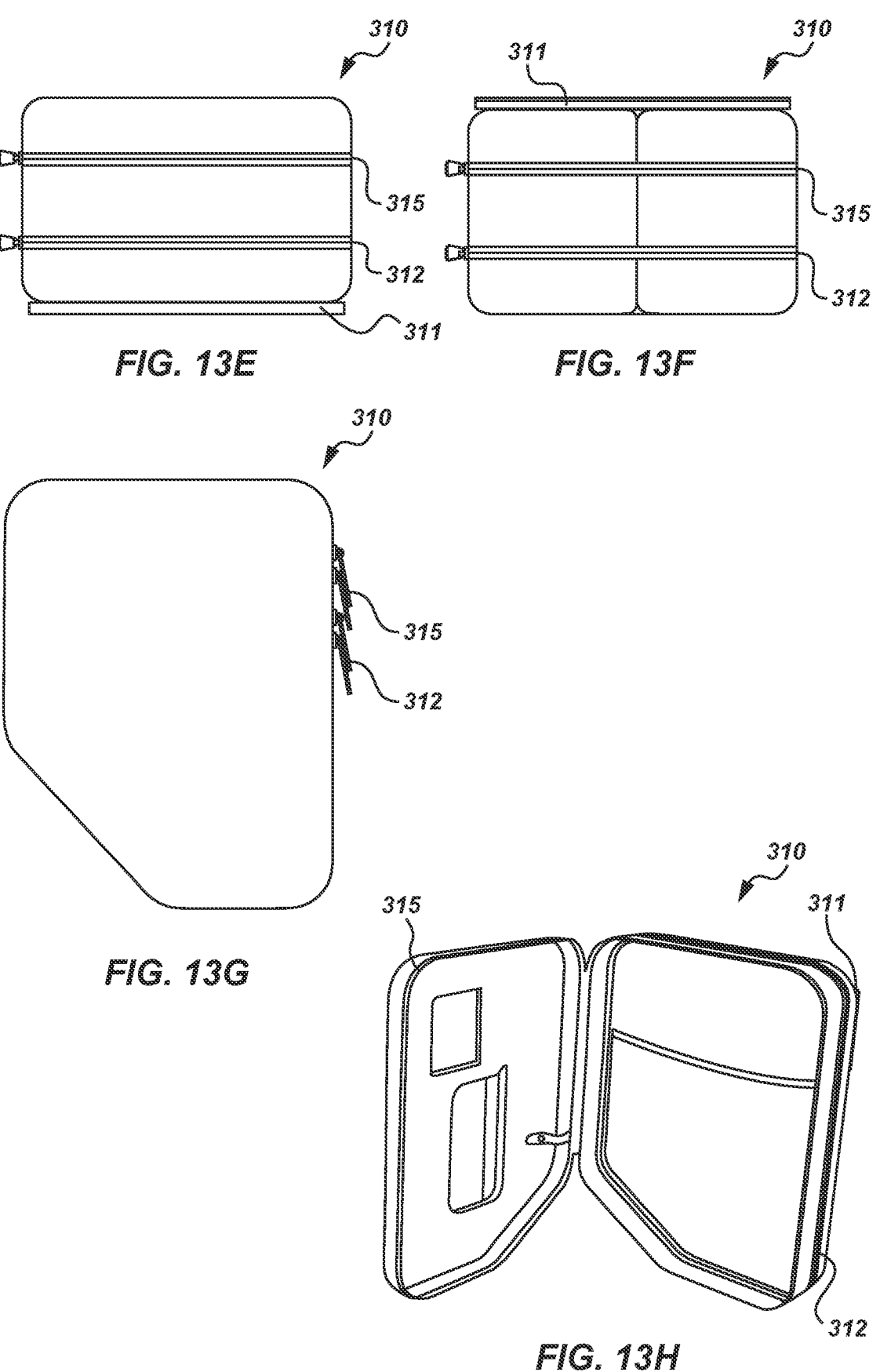
FIG. 13E illustrates a top view of the example storage bag depicted in FIG. 13A.
FIG. 13F illustrates a bottom view of the example storage bag depicted in FIG. 13A.
FIG. 13G illustrates a rear view of the example storage bag depicted in FIG. 13A.
FIG. 13H illustrates a perspective view of an interior of the example storage bag depicted in FIG. 13A.

FIG. 12 illustrates a perspective view of the port guard 200. In this example, the port guard 200 is a dual-molded, multi-material object (e.g., a two-part object that is composed of differing materials). In this example, the proximal portion 210 (sometimes referred to herein as the "base portion 210") of the port guard 200 is composed of a rigid material that is able to withstand impacts with or from external objects. The distal portion 220 of the port guard 200 is composed of a pliable, flexible, and/or elastic material that is relatively softer than the material of the proximal portion 210. The distal portion 220 is configured to flex to allow a user to comfortably access an ECG connector coupled to the ECG port 202 of the medical device 102. The pliable, flexible, and/or elastic material of the distal portion 220 can reduce damage caused by the collision of the port guard 200 and another object or person, since the material of the distal portion 220 is more flexible than the proximal portion 210 and is configured to flex and bend to absorb or reduce the impact. In an example, such as shown in FIG. 12, the material of the distal portion 220 of the port guard 200 extends over the interior of the proximal portion 210, which further assist in a user's comfort when interacting with an ECG connector that is coupled to the ECG port 202 of the medical device 102. The rigid material of the proximal portion 210 can prevent impacts to the coupled connector of an ECG cable 201 that might cause the connector to become loose or disconnected from the ECG port 202, while the relatively soft material of the distal portion 220 prevents the port guard 200 from damaging objects in the environment or injuring people while the medical device 102 is being moved.

FIG. 12 illustrates a perspective view of the port guard 200. In some examples, the proximal portion 210 is substantially rigid or stiff, such as by being composed of a rigid, durable material, such as a polymer material including a thermoplastic polymer, such as acrylonitrile butadiene styrene (ABS) plastic, or a similar material. Meanwhile, the distal portion 220 is relatively more flexible and softer than the material of the proximal portion 210, such as by being composed of a flexible, elastic material (e.g., a compliant rubber material). In the example of FIG. 12, the port guard 200 includes an annular-shaped protrusion made up of the proximal portion 210 and the distal portion 220, which extends a distance from the exterior surface of the medical device 102. The port guard 200 in FIG. 12 further includes a channel 212 defined in a side of the annular-shaped protrusion to accommodate and guide a cable, such as an ECG cable, that is coupled to the ECG port 202 of the medical device 102. Accordingly, the port guard 200 surrounds the port along three sides of the port. In this example, the port guard 200 includes a base plate 230 configured to be disposed on the exterior surface of the medical device 102, the proximal portion 210 extending from a front of the base plate 230. In this example, a groove 240 is defined in a portion of the base plate 230 (e.g., the groove 240 extends radially from the channel 212 to a side edge of the base plate 230), wherein the channel 212 and the groove 240 are configured to guide the cable when the connector of the cable is coupled to the port. The connector of the ECG cable 201 can direct the cable 201 orthogonal to the ECG port 202 and the cable 201 extends through the channel 212 and can rest in the groove 240. The port guard 200 can be removable from the medical device 102. In this example, the port guard 200 includes a tab 214 protruding from a back of the base plate 230 of the port guard 200 (e.g., in a direction toward the medical device 102). The tab 214 is configured to orient and locate the placement of the port guard 200 on the side of the medical device 102. The tab 214 is configured to interface with a complimentary slot on the medical device 102 that is proximal to the ECG port 202 to position and/or place the port guard 200 properly. In some examples, the port guard 200 includes a hollow post 216 disposed on the base plate 230 to place and orient the ECG port guard 200 on the medical device 102 and/or to couple the port guard 200 to the medical device 102. In an example, the hollow post 216 is configured to receive a fastener (e.g., a screw, a bolt, a pin, etc.) to releasably couple the port guard 200 to the medical device 102.

In some examples, the profile or shape of the port guard 200 is different from that shown in FIGS. 1A-1E and 12. The alternative profiles or shapes that the port guard 200 may possess can similarly extend beyond a connector coupled to the ECG port 202 of the medical device 102 to prevent the connector from being dislodged or disconnected from the ECG port 202 due to contact with an object or person in the external environment of the medical device 102. In some examples, the port guard 200 includes the groove 240 or other ECG cable-restraining feature to assist with organizing and managing the ECG cable 201 coupled to the ECG port 202 of the medical device 102. In an example, the port guard 200 includes the groove 240 into which a portion of the ECG cable 201 is configured to be pressed to manage or guide the ECG cable 201 from the port guard 200.

The port guard 200 may, in some examples, be used to shield or protect disconnection of therapy and/or monitoring cables from various ports of the medical device 102. Accordingly, the port guard 200 is configured to be coupled to the exterior of a medical device 102 and positioned about a port of the medical device 102, which may be any suitable type of port. Thus, the port guard 200 is configured to protect cables connected to any suitable port from being disconnected. In an example, a port guard, such as the port guard 200, is configured to be placed about a non-invasive blood pressure (NIBP) port, or about a temperature probe port, to prevent disconnection of the monitoring cables from this/ these port(s) of the medical device 102. Since the disconnection of one or more cables delays patient monitoring or treatment, the cable port guards reduce or prevent such delays by shielding or protecting various monitoring or therapy cable connections from becoming inadvertently disconnected.

Figures 14A, 14B:
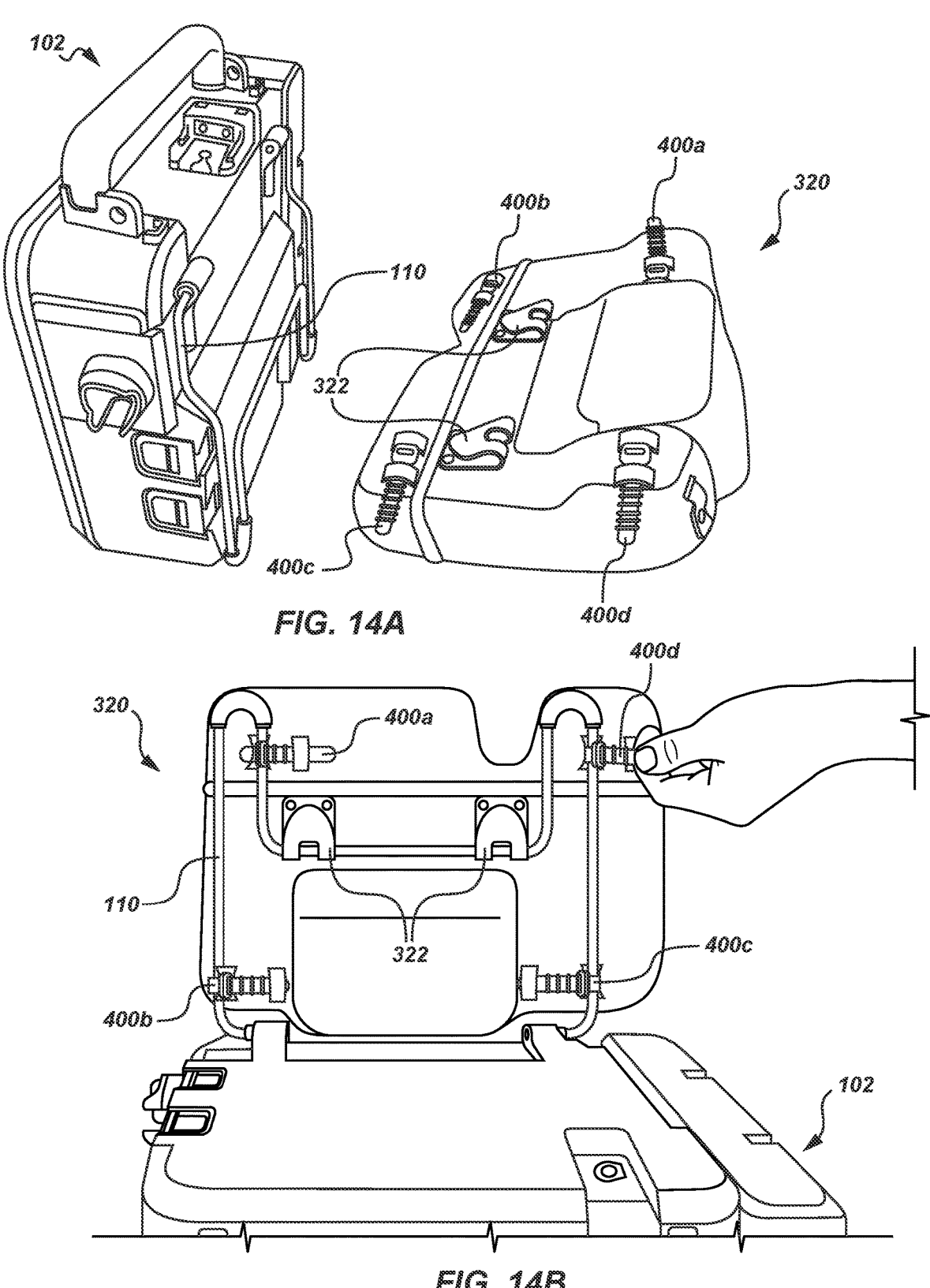
FIG. 14A illustrates a perspective view of an example rear storage bag having straps for coupling the rear storage bag to the example medical device.
FIG. 14B illustrates the rear storage bag depicted in FIG. 14A being coupled to the kickstand of the medical device using the straps.

FIG. 14A illustrates a perspective view of an example rear storage bag 320 having straps 400 for coupling the rear storage bag 320 to an example medical device 102, such as a defibrillator, here with a kickstand 110. FIGS. 14A and 14B depict the rear storage bag 320 as having four straps 400a, 400b, 400c, and 400d, but it is to be appreciated that the rear storage bag 320 may have fewer straps 400 or a greater number of straps 400. In some examples, the straps 400 are in the form of zip ties that includes a free end that a user passes through a looped end and pulls to tighten or cinch the strap 400 around the support 114 of the kickstand 110. Accordingly, in some examples, the straps 400 include spaced ridges along one side of the strap 400 to keep the strap 400 cinched once the strap 400 is tightened around the support 114 of the kickstand 110. In this example, the straps 400 are disposed on the rear of the rear storage bag 320, which is the side of the rear storage bag 320 adjacent to (and facing) the medical device 102. In this example, each of the four straps 400a, 400b, 400c, and 400d are positioned on the rear of the rear storage bag 320 adjacent to a corner of the rear storage bag 320. For example, two straps 400 (e.g., bottom straps 400b, 400c) are disposed at, or near, the bottom corners of the rear storage bag 320 and two straps 400 (e.g., top straps 400a, 400d) are disposed at, or near, the top corners of the rear storage bag 320. In this example, the clips 322 are positioned between the top straps 400a, 400d and the bottom straps 400b, 400c. In this configuration, the clips 322 are configured to clip onto (or slide over) a horizontal crossbar of the support 114 of the kickstand 110, the top straps 400a, 400d are configured to be tightened around the support 114 near the ends of the support 114 that couple to the hinges 112a, 112b, and the bottom straps 400b, 400c are configured to be tightened around the support near the feet 116a, 116b of the support 114, as depicted in FIG. 14B. In this manner, the rear storage bag 320 is configured to be coupled to the medical device 102 using the clips 322 and the straps 400, as depicted in FIG. 14B, such as by snapping the support 114 of the kickstand 110 into the clips 322 and securing the straps 400 to the support 114 of the kickstand 110. The straps 400 prevent the rear storage bag 320 from sliding and/or rotating out of alignment with the medical device 102 to which the rear storage bag 320 is coupled, and the straps 400 help mitigate damage to the accessories stored in the rear storage bag 320.

Next follow example clauses reciting features and options applicable in view of the defibrillator, the medical device, the method, the port guard, the kickstand, and the storage bag.

EXAMPLE CLAUSES

1. A defibrillator including: an accessory cable port disposed on an exterior surface of the defibrillator and configured to receive a connector of an accessory cable; and a port guard partially surrounding the accessory cable port and protruding from the exterior surface of the defibrillator.

2. The defibrillator of clause 1, wherein the port guard includes: a proximal portion made of a first material; and a distal portion made of a second material different than the first material.

3. The defibrillator of clause 2, wherein the first material is less flexible than the second material.

4. The defibrillator of any one of clauses 1 to 3, wherein the accessory cable port is an electrocardiogram (ECG) port, and wherein the accessory cable is an ECG cable.

5. The defibrillator of any one of clauses 1 to 4, wherein the port guard protrudes beyond an attachment point between the connector and the accessory cable when the connector is coupled to the accessory cable port.

6. The defibrillator of any one of clauses 1 to 5, wherein the port guard has a channel defined therein to guide the accessory cable when the connector is coupled to the accessory cable port.

7. The defibrillator of any one of clauses 1 to 6, wherein the port guard further includes a tab protruding into a slot defined in the exterior surface of the defibrillator.

8. The defibrillator of any one of clauses 1 to 7, wherein the port guard further includes a hollow post configured to receive a fastener to releasably couple the port guard to the defibrillator.

9. The defibrillator of any one of clauses 1 to 8, further including a storage bag coupled to a portion of the defibrillator, and wherein: the port guard is disposed within an opening defined in a portion of the storage bag; the port guard extends into an interior of the storage bag configured to store an accessory; and the opening defined in the portion of the storage bag is configured to allow the accessory to be coupled to the accessory cable port while the accessory is stored within the interior of the storage bag and while the storage bag is closed.

10. A port guard configured to be positioned about a port of a defibrillator, the port guard including: a proximal portion having an annular shape and configured to protrude from an exterior surface of the defibrillator when the port guard is coupled to the defibrillator, the proximal portion made of a first material; and a distal portion disposed on the proximal portion, the distal portion having the annular shape and configured to protrude from the proximal portion, the distal portion made of a second material different than the first material.

11. The port guard of clause 10, wherein the first material is stiffer than the second material.

12. The port guard of clause 10 or 11, wherein the port guard further includes: a base plate configured to be disposed on the exterior surface of the defibrillator, the proximal portion protruding from a front of the base plate; and a tab protruding from a back of the base plate and configured to position the port guard when the port guard is being coupled to the defibrillator.

13. The port guard of clause 12, wherein the port guard has: a channel defined in a side of the proximal portion and the distal portion; and a groove defined in a portion of the base plate, wherein the channel and the groove are configured to guide a cable when a connector of the cable is coupled to the port.

14. The port guard of clause 12 or 13, wherein the port guard further includes a hollow post disposed on the base plate and configured to receive a fastener to releasably couple the port guard to the defibrillator.

15. A defibrillator including: a port disposed on an exterior surface of the defibrillator and configured to receive a connector of an accessory of the defibrillator; a port guard partially surrounding the port and protruding from the exterior surface of the defibrillator; and a storage bag coupled to a portion of the defibrillator, the storage bag being openable and closable and including: an interior configured to store the accessory; and an opening defined in a portion of the storage bag, the port guard disposed within the opening, and the opening configured to allow the accessory to be coupled to the port while the accessory is stored within the interior of the storage bag and while the storage bag is closed.

16. The defibrillator of clause 15, wherein the port guard surrounds the port along three sides of the port.

17. The defibrillator of clause 15 or 16, wherein the port guard includes: a proximal portion made of a first material; and a distal portion made of a second material different than the first material.

18. The defibrillator of any one of clauses 15 to 17, wherein the port is an electrocardiogram (ECG) port, and wherein the cable is an ECG cable.

19. The defibrillator of any one of clauses 15 to 18, wherein the port guard includes an annular-shaped protrusion that extends a distance from the exterior surface of the defibrillator.

20. The defibrillator of any one of clauses 15 to 19, wherein the port guard further includes a tab protruding into a slot defined in the exterior surface of the defibrillator.

21. The defibrillator of any one of clauses 15 to 20, wherein the port guard further includes a hollow post configured to receive a fastener to releasably couple the port guard to the defibrillator.

22. A defibrillator including: a display disposed on a front of the defibrillator; and a kickstand coupled to a back of the defibrillator, the kickstand including: a first hinge mounted to the back of the defibrillator within an upper left quadrant of the back of the defibrillator; a second hinge mounted to the back of the defibrillator within an upper right quadrant of the back of the defibrillator; and a support that is movable relative to the defibrillator to transition the kickstand between a collapsed position and an extended position, the support including: a first end rotatably coupled to the first hinge; a second end rotatably coupled to the second hinge; a first foot coupled to the first end of the support and disposed adjacent to a lower left quadrant of the back of the defibrillator when the kickstand is in the collapsed position; and a second foot coupled to the second end of the support and disposed adjacent to a lower right quadrant of the back of the defibrillator when the kickstand is in the collapsed position, wherein the first foot and the second foot are configured to contact a surface on which the defibrillator rests when the kickstand is in the extended position.

23. The defibrillator of clause 22, wherein: a profile of a rear surface of the defibrillator is contoured; and the support includes a bent rod that substantially conforms to the profile of the rear surface of the defibrillator.

24. The defibrillator of clause 22 or 23, wherein: the support further includes: a first hinge element disposed at the first end of the support, the first hinge element having a substantially circular cross section; and a second hinge element disposed at the second end of the support, the second hinge element having a substantially circular cross section; the first hinge includes a first opening that is substantially circular, the first hinge element being disposed within the first opening; and the second hinge includes a second opening that is substantially circular, the second hinge element being disposed within the second opening.

25. The defibrillator of any one of clauses 22 to 24, wherein the extended position is a maximum extended position, and wherein the support is movable relative to the defibrillator to position the kickstand at an intermediate extended position between the collapsed position and the maximum extended position.

26. A defibrillator including: a display disposed on a front of the defibrillator; and a kickstand coupled to a back of the defibrillator, the kickstand including a support that is movable relative to the defibrillator to transition the kickstand between a collapsed position and an extended position, the support including: a first end pivotably coupled to the back of the defibrillator; a second end pivotably coupled to the back of the defibrillator; a first foot coupled to the first end of the support; and a second foot coupled to the second end of the support, wherein the first foot and the second foot are configured to contact a surface on which the defibrillator rests when the kickstand is in the extended position.

27. The defibrillator of clause 26, wherein: a profile of a rear surface of the defibrillator is contoured; and the support includes a bent rod that substantially conforms to the profile of the rear surface of the defibrillator.

28. The defibrillator of clause 26 or 28, wherein the first foot is u-shaped, and wherein the second foot is u-shaped.

29. The defibrillator of any one of clauses 26 to 28, wherein: the kickstand further includes: a first hinge mounted to the back of the defibrillator within an upper left quadrant of the back of the defibrillator, the first hinge including a first opening; a second hinge mounted to the back of the defibrillator within an upper right quadrant of the back of the defibrillator, the second hinge including a second opening; and the first end of the support includes a first hinge element that is disposed within the first opening; and the second end of the support includes a second hinge element that is disposed within the second opening.

30. The defibrillator of any one of clauses 26 to 29, wherein the extended position is a maximum extended position, and wherein the support is movable relative to the defibrillator to position the kickstand at an intermediate extended position between the collapsed position and the maximum extended position.

31. A kickstand for a defibrillator, the kickstand including: a first hinge configured to be mounted to a back of the defibrillator; a second hinge configured to be mounted to the back of the defibrillator; and a support that is configured to move relative to the defibrillator to transition the kickstand between a collapsed position and an extended position, the support including: a first end configured to be rotatably coupled to the first hinge; a second end configured to be rotatably coupled to the second hinge; and a first foot coupled to the first end of the support; and a second foot coupled to the second end of the support, wherein the first foot and the second foot are configured to contact a surface on which the defibrillator rests when the kickstand is in the extended position.

32. The kickstand of clause 31, wherein the support includes a bent rod that substantially conforms to a contoured profile of a rear surface of the defibrillator.

33. The kickstand of clause 31 or 32, wherein: the first hinge includes a first opening; the second hinge includes a second opening; the first end of the support includes a first hinge element that is configured to be inserted into the first opening; and the second end of the support includes a second hinge element that is configured to be inserted into the second opening.

34. The kickstand of any one of clauses 31 to 33, wherein the support includes a bent rod that is configured to extend around a power connector on the back of the defibrillator to avoid obstructing the power connector.

35. A defibrillator including: a port disposed on an exterior surface of the defibrillator and configured to receive a connector of an accessory of the defibrillator; and a storage bag coupled to a portion of the defibrillator, the storage bag being openable and closable and including: an interior configured to store the accessory; and an opening defined in a portion of the storage bag, the opening configured to allow the accessory to be coupled to the port while the accessory is stored within the interior of the storage bag and while the storage bag is closed.

36. The defibrillator of clause 35, wherein: the accessory includes a printer; the storage bag includes a printer bag; and the portion of the defibrillator includes a back of the defibrillator.

37. The defibrillator of clause 36, wherein: the printer bag includes clips disposed on an exterior surface of the printer bag; the defibrillator further includes a kickstand coupled to the back of the defibrillator; and the clips are configured to clip onto a portion of the kickstand.

38. The defibrillator of any one of clauses 35 to 37, wherein the port is aligned with the opening defined in the portion of the storage bag when the storage bag is coupled to the portion of the defibrillator.

39. The defibrillator of any one of clauses 35 to 38, wherein: the storage bag includes a side storage bag; and the portion of the defibrillator includes a side of the defibrillator disposed between a front of the defibrillator and a back of the defibrillator.

40. The defibrillator of clause 39, further including a port guard positioned about the port, and wherein, when the storage bag is coupled to the side of the defibrillator, the port guard is disposed within the opening defined in the portion of the storage bag; and extends into the interior of the storage bag.

41. The defibrillator of clause 39 or 40, wherein: the portion of the storage bag in which the opening is defined is a front cover of the storage bag; and the opening is configured to allow a cable of the accessory to pass from the interior of the storage bag through the front cover to couple the accessory to the port.

42. A defibrillator including: a display disposed on a front of the defibrillator; and a storage bag coupled to a portion of the defibrillator other than the front of the defibrillator, the storage bag being openable and closable and including: an interior configured to store an accessory of the defibrillator; and an opening defined in a portion of the storage bag, the opening configured to allow the accessory to be coupled to the defibrillator while the accessory is stored within the interior of the storage bag and while the storage bag is closed.

43. The defibrillator of clause 42, wherein: the accessory includes a printer; the storage bag includes a printer bag; and the portion of the defibrillator includes a back of the defibrillator.

44. The defibrillator of clause 43, wherein: the printer bag includes clips disposed on an exterior surface of the printer bag; the defibrillator further includes a kickstand coupled to the back of the defibrillator; and the clips are configured clip onto a portion of the kickstand.

45. The defibrillator of any one of clauses 42 to 44, wherein a port disposed on the defibrillator is aligned with the opening defined in the portion of the storage bag when the storage bag is coupled to the portion of the defibrillator.

46. The defibrillator of any one of clauses 42 to 45, wherein: the storage bag includes a side storage bag; and the portion of the defibrillator includes a side of the defibrillator disposed between the front of the defibrillator and a back of the defibrillator.

47. The defibrillator of clause 46, further including a port guard positioned about a port disposed on the defibrillator, and wherein, when the storage bag is coupled to the side of the defibrillator, the port guard: is disposed within the opening defined in the portion of the storage bag; and extends into the interior of the storage bag.

48. The defibrillator of clause 46 or 47, wherein: the portion of the storage bag in which the opening is defined is a front cover of the storage bag; and the opening is configured to allow a cable of the accessory to pass from the interior of the storage bag through the front cover to couple the accessory to the defibrillator.

49. A storage bag for a defibrillator, the storage bag being openable and closable, configured to couple to a portion of the defibrillator, and including: an interior configured to store an accessory of the defibrillator; and an opening defined in a portion of the storage bag, the opening configured to allow the accessory to be coupled to the defibrillator while the accessory is stored within the interior of the storage bag and while the storage bag is closed.

50. The storage bag of clause 49, wherein: the accessory includes a printer; the storage bag includes a printer bag; and the portion of the defibrillator includes a back of the defibrillator.

51. The storage bag of clause 50, wherein: the printer bag includes clips disposed on an exterior surface of the printer bag; the defibrillator includes a kickstand coupled to the back of the defibrillator; and the clips are configured to clip onto a portion of the kickstand within the clips.

52. The storage bag of any one of clauses 49 to 51, wherein a port disposed on the defibrillator is aligned with the opening defined in the portion of the storage bag when the storage bag is coupled to the portion of the defibrillator.

53. The storage bag of any one of clauses 49 to 52, wherein: the storage bag includes a side storage bag; and the portion of the defibrillator includes a side of the defibrillator disposed between a front of the defibrillator and a back of the defibrillator.

54. The storage bag of clause 53, wherein: the portion of the storage bag in which the opening is defined is a front cover of the storage bag; and the opening is configured to allow a cable of the accessory to pass from the interior of the storage bag through the front cover to couple the accessory to the defibrillator.

55. A defibrillator including: a display disposed on a front of the defibrillator; a port disposed on an exterior surface of the defibrillator and configured to receive a connector of a cable; a port guard positioned about the port and protruding from the exterior surface of the defibrillator; a storage bag coupled to a portion of the defibrillator other than the front of the defibrillator, the storage bag being openable and closable and including an interior configured to store an accessory of the defibrillator; and a kickstand coupled to a back of the defibrillator, the kickstand including a support that is movable relative to the defibrillator to transition the kickstand between a collapsed position and an extended position.

56. The defibrillator of clause 55, wherein the support includes: a first end pivotably coupled to the back of the defibrillator; a second end pivotably coupled to the back of the defibrillator; a first foot coupled to the first end of the support; and a second foot coupled to the second end of the support, wherein the first foot and the second foot are configured to contact a surface on which the defibrillator rests when the kickstand is in the extended position.

57. The defibrillator of clause 55 or 56, wherein: a profile of a rear surface of the defibrillator is contoured; and the support includes a bent rod that substantially conforms to the profile of the rear surface of the defibrillator.

58. The defibrillator of any one of clauses 55 to 57, wherein the port guard includes: a proximal portion made of a first material; and a distal portion made of a second material different than the first material.

59. The defibrillator of any one of clauses 55 to 58, wherein the port is an electrocardiogram (ECG) port, and wherein the cable is an ECG cable.

60. The defibrillator of any one of clauses 55 to 59, wherein the storage bag further includes an opening defined in a portion of the storage bag, the opening configured to allow the accessory to be coupled to the defibrillator while the accessory is stored within the interior of the storage bag and while the storage bag is closed.

61. The defibrillator of clause 60, wherein the port is aligned with the opening defined in the portion of the storage bag when the storage bag is coupled to the portion of the defibrillator.

62. A defibrillator including: a display disposed on a front of the defibrillator; a port disposed on an exterior surface of the defibrillator and configured to receive a connector of a cable; and at least one of: a port guard positioned about the port and protruding from the exterior surface of the defibrillator; a storage bag coupled to a portion of the defibrillator other than the front of the defibrillator, the storage bag being openable and closable and including an interior configured to store an accessory of the defibrillator; or a kickstand coupled to a back of the defibrillator, the kickstand including a support that is movable relative to the defibrillator to transition the kickstand between a collapsed position and an extended position, the support including: a first end pivotably coupled to the back of the defibrillator; a second end pivotably coupled to the back of the defibrillator; a first foot coupled to the first end of the support; and a second foot coupled to the second end of the support, wherein the first foot and the second foot are configured to contact a surface on which the defibrillator rests when the kickstand is in the extended position.

63. The defibrillator of clause 62, wherein the defibrillator includes the port guard and the storage bag.

64. The defibrillator of clause 62 or 63, wherein the defibrillator includes the port guard and the kickstand.

65. The defibrillator of any one of clauses 62 to 64, wherein the defibrillator includes the storage bag and the kickstand.

66. The defibrillator of any one of clauses 62 to 65, wherein: the defibrillator includes the kickstand; a profile of a rear surface of the defibrillator is contoured; and the support includes a bent rod that substantially conforms to the profile of the rear surface of the defibrillator.

67. The defibrillator of any one of clauses 62 to 66, wherein: the defibrillator includes the port guard; and the port guard includes: a proximal portion made of a first material; and a distal portion made of a second material different than the first material.

68. The defibrillator of any one of clauses 62 to 67, wherein: the defibrillator includes the storage bag; and the storage bag further includes an opening defined in a portion of the storage bag, the opening configured to allow the accessory to be coupled to the defibrillator while the accessory is stored within the interior of the storage bag and while the storage bag is closed.

69. The defibrillator of clause 68, wherein the port is aligned with the opening defined in the portion of the storage bag when the storage bag is coupled to the portion of the defibrillator.

70. A medical device including: a display disposed on a front of the medical device; a port disposed on an exterior surface of the medical device and configured to receive a connector of a cable; and at least one of: a port guard positioned about the port and protruding from the exterior surface of the medical device; a storage bag coupled to a portion of the medical device other than the front of the medical device, the storage bag being openable and closable and including an interior configured to store an accessory of the medical device; or a kickstand coupled to a back of the medical device, the kickstand including a support that is movable relative to the medical device to transition the kickstand between a collapsed position and an extended position, the support including: a first end pivotably coupled to the back of the medical device; a second end pivotably coupled to the back of the medical device; a first foot coupled to the first end of the support; and a second foot coupled to the second end of the support, wherein the first foot and the second foot are configured to contact a surface on which the medical device rests when the kickstand is in the extended position.

71. The medical device of clause 70, wherein the medical device includes the port guard and the storage bag.

72. The medical device of clause 70 or 71, wherein the medical device includes the port guard and the kickstand.

73. The medical device of any one of clauses 70 to 72, wherein the medical device includes the storage bag and the kickstand.

74. The medical device of any one of clauses 70 to 73, wherein: the medical device includes the storage bag; the storage bag further includes an opening defined in a portion of the storage bag, the opening configured to allow the accessory to be coupled to the medical device while the accessory is stored within the interior of the storage bag and while the storage bag is closed; and the port is aligned with the opening defined in the portion of the storage bag when the storage bag is coupled to the portion of the medical device.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof. For the purpose of clarity and a concise description features are described herein as part of the same or separate embodiments, however, alternative embodiments having combinations of all or some, or only some, of the features described in these separate embodiments are also envisaged.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventor expects skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

The invention claimed is:

1. A defibrillator comprising:
a port disposed on an exterior surface of the defibrillator and configured to receive a connector of an accessory of the defibrillator;
a power connector disposed on a back of the defibrillator, wherein the back of the defibrillator is opposite a front of the defibrillator, the front of the defibrillator having a display; and
a storage bag coupled to the back of the defibrillator, the storage bag being openable and closable and comprising:
an interior configured to store the accessory;
an opening defined in a portion of the storage bag, the opening configured to allow the accessory to be coupled to the port while the accessory is stored within the interior of the storage bag and while the storage bag is closed; and a notch defined in a base of the storage bag, the notch configured to allow access to the power connector while the storage bag is coupled to the back of the defibrillator.

2. The defibrillator of claim 1, wherein the accessory comprises a printer.

3. The defibrillator of claim 1, wherein:

the storage bag comprises clips disposed on an exterior surface of the storage bag;

the defibrillator further comprises a kickstand coupled to the back of the defibrillator; and the clips are configured to clip onto a portion of the kickstand.

4. The defibrillator of claim 1, wherein the port is aligned with the opening defined in the portion of the storage bag when the storage bag is coupled to the back of the defibrillator.

5. The defibrillator of claim 1, wherein the storage bag is a rear storage bag, the defibrillator further comprising a side storage bag coupled to a side of the defibrillator disposed between the front of the defibrillator and the back of the defibrillator.

6. The defibrillator of claim 5, wherein the accessory is a first accessory, wherein the port is a first port, and wherein the opening is a first opening, the defibrillator further comprising:

a second port disposed on the side of the defibrillator and configured to receive a connector of a second accessory of the defibrillator; and a port guard positioned about the second port, wherein the side storage bag comprises a second opening defined in a portion of the side storage bag, the second opening configured to allow the second accessory to be coupled to the second port while the second accessory is stored within an interior of the side storage bag and while the side storage bag is closed, and wherein, when the side storage bag is coupled to the side of the defibrillator, the port guard:

is disposed within the second opening; and extends into the interior of the side storage bag.

7. The defibrillator of claim 5, wherein the accessory is a first accessory, wherein the port is a first port, and wherein the opening is a first opening, the defibrillator further comprising:

a second port disposed on the exterior surface of the defibrillator and configured to receive a connector of a second accessory of the defibrillator, wherein the side storage bag comprises a second opening defined in a front cover of the side storage bag, the second opening configured to allow a cable of the second accessory to pass from an interior of the side storage bag through the front cover to couple the second accessory to the second port while the second accessory is stored within the interior of the side storage bag and while the side storage bag is closed.

8. A defibrillator comprising:

a display disposed on a front of the defibrillator;

a power connector disposed on a back of the defibrillator; and a storage bag coupled to the back of the defibrillator, the storage bag being openable and closable and comprising:

an interior configured to store an accessory of the defibrillator;

an opening defined in a portion of the storage bag, the opening configured to allow the accessory to be coupled to the defibrillator while the accessory is stored within the interior of the storage bag and while the storage bag is closed; and a notch defined in a base of the storage bag, the notch configured to allow access to the power connector while the storage bag is coupled to the back of the defibrillator.

9. The defibrillator of claim 8, wherein the accessory comprises a printer.

10. The defibrillator of claim 8, wherein:

the storage bag comprises clips disposed on an exterior surface of the storage bag;

the defibrillator further comprises a kickstand coupled to the back of the defibrillator; and the clips are configured to clip onto a portion of the kickstand.

11. The defibrillator of claim 8, wherein a port disposed on the defibrillator is aligned with the opening defined in the portion of the storage bag when the storage bag is coupled to the back of the defibrillator.

12. The defibrillator of claim 8, wherein the storage bag is a rear storage bag, the defibrillator further comprising a side storage bag coupled to a side of the defibrillator disposed between the front of the defibrillator and the back of the defibrillator.

13. The defibrillator of claim 12, wherein the accessory is a first accessory, and wherein the opening is a first opening, the defibrillator further comprising:

a port disposed on the side of the defibrillator and configured to receive a connector of a second accessory of the defibrillator; and a port guard positioned about the port, wherein the side storage bag comprises a second opening defined in a portion of the side storage bag, the second opening configured to allow the second accessory to be coupled to the port while the second accessory is stored within an interior of the side storage bag and while the side storage bag is closed, and wherein, when the side storage bag is coupled to the side of the defibrillator, the port guard:

is disposed within the second opening; and extends into the interior of the side storage bag.

14. The defibrillator of claim 12, wherein the accessory is a first accessory, and wherein the opening is a first opening, the defibrillator further comprising:

a port disposed on an exterior surface of the defibrillator and configured to receive a connector of a second accessory of the defibrillator, wherein the side storage bag comprises a second opening defined in a front cover of the side storage bag, the second opening configured to allow a cable of the second accessory to pass from an interior of the side storage bag through the front cover to couple the second accessory to the port while the second accessory is stored within the interior of the side storage bag and while the side storage bag is closed.

* * * * *